US012161616B2

(12) United States Patent
Smith et al.

(10) Patent No.: US 12,161,616 B2
(45) Date of Patent: *Dec. 10, 2024

(54) COMBINATION THERAPY COMPRISING AN OMEGA-3 FATTY ACID, A FOLATE SPECIES AND A VITAMIN B12 SPECIES

(71) Applicant: Oxford University Innovation Limited, Summertown (GB)

(72) Inventors: David Smith, Oxford (GB); Fredrik Jerneren, Oxford (GB); Helga Refsum, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 151 days.

This patent is subject to a terminal disclaimer.

(21) Appl. No.: 17/194,517

(22) Filed: Mar. 8, 2021

(65) Prior Publication Data

US 2021/0196663 A1 Jul. 1, 2021

Related U.S. Application Data

(63) Continuation of application No. 15/127,717, filed as application No. PCT/GB2015/050786 on Mar. 17, 2015, now Pat. No. 10,966,947.

(30) Foreign Application Priority Data

Mar. 20, 2014 (GB) ..................................... 1405033

(51) Int. Cl.
| A61K 31/202 | (2006.01) |
| A61K 9/00 | (2006.01) |
| A61K 31/14 | (2006.01) |
| A61K 31/205 | (2006.01) |
| A61K 31/232 | (2006.01) |
| A61K 31/4415 | (2006.01) |
| A61K 31/519 | (2006.01) |
| A61K 31/714 | (2006.01) |
| A61P 25/28 | (2006.01) |

(52) U.S. Cl.
CPC .......... *A61K 31/202* (2013.01); *A61K 9/0053* (2013.01); *A61K 31/14* (2013.01); *A61K 31/205* (2013.01); *A61K 31/232* (2013.01); *A61K 31/4415* (2013.01); *A61K 31/519* (2013.01); *A61K 31/714* (2013.01); *A61P 25/28* (2018.01)

(58) Field of Classification Search
CPC ...... A61P 9/0053; A61P 25/28; A61K 31/202; A61K 31/14; A61K 31/205; A61K 31/232; A61K 31/4415; A61K 31/519; A61K 31/714

See application file for complete search history.

(56) References Cited

U.S. PATENT DOCUMENTS

| 2006/0247163 A1 | 11/2006 | McMahon et al. |
| 2013/0142769 A1 | 6/2013 | Smith et al. |
| 2013/0230592 A1 | 9/2013 | Terreaux et al. |
| 2015/0031653 A1 | 1/2015 | Mathisen et al. |

FOREIGN PATENT DOCUMENTS

| EP | 1800675 A1 | 6/2007 |
| FR | 2979543 A1 | 3/2013 |
| WO | WO 01/03696 A1 | 1/2001 |
| WO | WO 01/84961 A2 | 11/2001 |
| WO | WO 2009/002148 A1 | 12/2008 |
| WO | WO 2011/143587 A1 | 11/2011 |
| WO | 2012001336 | 1/2012 |
| WO | WO 2012/049222 A3 | 4/2012 |
| WO | WO 2012/091542 A1 | 7/2012 |
| WO | WO 2013/066152 A1 | 5/2013 |

OTHER PUBLICATIONS

Oxford English Dictionary, s.v. "develop, v.", Sep. 2023. <https://doi.org/10.1093/OED/4524741115> (Year: 2023).*
van Soest, Annick P. M. et al., European Journal of Nutrition, "DHA status influences effects of B-vitamin supplementation on cognitive ageing: a post-hoc analysis of the B-proof trial", 2022, vol. 61, pp. 3731-3739 (Year: 2022).*
Pini et al. "Brain atrophy in Alzheimer's Disease and aging" Ageing Research Reviews, 2016, 24 pages.
Jack et al. "Steps to standardization and validation of hippocampal volumetry as a biomarker in clinical trials and diagnostic criterion for Alzheimer's disease" Alzheimer's & Dementia: The Journal of the Alzheimer'sAssociation, 7(4) 22 pages (2011).
Tabatabaei-Jafari et al. "Cerebral atrophy in mild cognitive impairment: A systematic review with meta-analysis" Alzheimer's & Dementia: Diagnosis, Assessment & Disease Monitoring, 1(4):487-504 (2015).
European Examination Report corresponding to EP 15713556.7, dated Jul. 9, 2019. 7 pp.
Oulhaj et al. "Omega-3 Fatty Acid Status Enhances the Prevention of Cognitive Decline by B Vitamins in Mild Cognitive Impairment" Journal of Alzheimer's Disease, 50:547-557 (2016).

(Continued)

*Primary Examiner* — Bahar Craigo
(74) *Attorney, Agent, or Firm* — Myers Bigel, P.A.

(57) ABSTRACT

The present invention provides a combined therapy comprising the use of one or more omega-3 fatty acids and one or more B vitamins and for treating cognitive impairment, such cognitive impairment disorders include, especially but not exclusively, Mild Cognitive Impairment (MCI) and Alzheimer's disease (AD). The present invention also provides a treatment for individuals suffering from cognitive impairment disorders that occur as a result of brain or cerebral atrophy, the invention includes inter alia methods of treating and/or reducing progression of brain atrophy and pharmaceutical compositions and nutritional supplements therefor.

6 Claims, 2 Drawing Sheets

(56) References Cited

OTHER PUBLICATIONS

Chiu et al., "The effects of omega-3 fatty acids monotherapy in Alzheimer's disease and mild cognitive impairment: A preliminary randomized double-blind placebo-controlled study" Progress in Neuro-sychopharmacology & Biological Psychiatry, 32:1538-1544 (2008).

Freund-Levi et al. "w-3 Fatty Acid Treatment in 174 Patients With Mild to Moderate Alzheimer Disease: OmegAD Study" Arch Neurol, 63:1402-1410 (2006).

Kotani et al. "Dietary supplementation of arachidonic and docosahexaenoic acids improves cognitive dysfunction" Neuroscience Research, 56:159-164 (2006).

Ganguly et al. "Role of homocysteine in the development of cardiovascular disease" Nutrition Journal, 14(6):1-10 (2015).

Jerneren F et al. Brain atrophy in cognitively impaired elderly: the importance of long-chain omega-3 fatty acids and B vitamin status in a randomized controlled trial. Am J Clin Nutr. 2015: 102: 215-21.

Aisen et al. "A Pilot Study of Vitamins to Lower Plasma Homocysteine Levels in Alzheimer Disease" *The American Journal of Geriatric Psychiatry* 11(2):246-249 (2003).

Aisen et al. "High Dose B Vitamin Supplementation and Cognitive Decline in Alzheimer's Disease: A Randomized Controlled Trial" *The Journal of the American Medical Association* 300(15):1774-1783 (2008).

Bagepally et al. "Relationship of Clinical and Cognitive Variables with Brain Morphometric Abnormalities in Alzheimer's Disease: a Voxel Based Morphometric Study Using 3-Tesla MRI" *Aging and Disease* 4(5):235-243 (2013).

Bradley et al. "Serial brain MRI at 3-6 month intervals as a surrogate marker for Alzheimer's disease" *The British Journal of Radiology* 75:506-513 (2002).

Bryan et al. "Short-Term Folate, Vitamin B-12 or Vitamin B-6 Supplementation Slightly Affects Memory Performance But Not Mood in Women of Various Ages" *The Journal of Nutrition* 132(6):1345-1356 (2002).

Burns et al. "Phase 1 Clinical Study of Fish Oil Fatty Acid Capsules for Patients with Cancer Cachexia: Cancer and Leukemia Group B Study 9473" *Clinical Cancer Research* 5:3942-3947 (1999).

Calvaresi et al. "B Vitamins, Cognition, and Aging: A Review" *Journal of Gerontology: Psychological Sciences* 56B(6):P327-P339 (2001).

Cardenas et al. "Brain atrophy associated with baseline and longitudinal measures of cognition" *Neurobiology of Aging* 32:572-580 (2011).

De Jager et al. "Cognitive and clinical outcomes of homocysteine-lowering B-vitamin treatment in mild cognitive impairment: a randomized controlled trial" *International Journal of Geriatric Psychiatry* 27(6):592-600 (2012).

Douaud et al. "Preventing Alzheimer's disease-related gray matter atrophy by B-vitamin treatment" *Proceedings of the National Academy of Sciences USA* 110(23):9523-9528 (2013).

Durga et al. "Effect of 3-year folic acid supplementation on cognitive function in older Adults in the FACIT trial: a randomised, double blind, controlled trial" *Lancet* 369(9557):208-216 (2007).

Folstein et al. "Mini-mental state" *Journal of Psychiatric Research* 12(3):189-198 (1975) (Abstract only).

Fox et al. "Correlation between rates of brain atrophy and cognitive decline in AD" *Neurology* 52(8):1687-1689 (1999).

Gewa et al. "Dietary micronutrients are associated with higher cognitive function gains among primary school children in rural Kenya" *British Journal of Nutrition* 101:1378-1387 (2009).

Huang et al. "Omega-3 Fatty Acids, Cognitive Decline, and Alzheimer's Disease: A Critical Review and Evaluation of the Literature" *Journal of Alzheimer's Disease* 21(3):673-690 (2010).

Huang et al. "High consumption of Ω-3 polyunsaturated fatty acids decrease plasma homocysteine: A meta-analysis of randomised, placebo-controlled trials" *Nutrition* 27(9):863-867 (2011).

Jack et al. "Comparison of different MRI brain atrophy rate measures with clinical disease progression in AD" *Neurology* 62(4):591-600 (2004).

Jack et al. "Brain atrophy rates predict subsequent clinical conversion in normal elderly and amnestic MCI" *Neurology* 65(8):1227-1231 (2005).

Kang et al. "A trial of B vitamins and cognitive function among women at high risk of cardiovascular disease" *The American Journal of Clinical Nutrition* 88(6):1602-1610 (2008).

Kluger et al. "Neuropsychological Prediction of Decline to Dementia in Nondemented Elderly" *Journal of Geriatric Psychiatry and Neurology* 12:168-179 (1999).

Lehmann et al. "Vitamin $B_{12}$-$B_6$-Folate Treatment Improves Blood-Brain Barrier Function in Patients with Hyperhomocysteinaemia and Mild Cognitive Impairment" *Dementia and Geriatric Cognitive Disorders* 16:145-150 (2003).

Mehmetoglu et al. "Plasma ω-3 fatty acid levels negatively and ω-6 fatty acid levels positively associated with other cardiovascular risk factors including homocysteine in severe obese subjects" *Asia Pacific Journal of Clinical Nutrition* 21(4):519-525 (2012).

Petersen et al. "Mild Cognitive Impairment: Ten Years Later" *Archives of Neurology* 66(12):1447-1455 (2009).

Pottala et al. "Higher RBC EPA + DHA corresponds with larger total brain and hippocampal volumes" *Neurology* 82:435-442 (2014).

Quinn et al. "Docosahexaenoic Acid Supplementation and Cognitive Decline in Alzheimer Disease: A Randomized Trial" *The Journal of the American Medical Association* 304(17):1903-1911 (2010).

Ravaglia et al. "Homocysteine and folate as risk factors for dementia and Alzheimer disease" *The American Journal of Clinical Nutrition* 82(3):636-643 (2005).

Risacher et al. "Baseline MRI Predictors of Conversion from MCI to Probable AD in the ADNI Cohort" *Current Alzheimer Research* 6(4):347-361 (2009).

Risacher et al. "Longitudinal MRI atrophy biomarkers: Relationship to conversion in the ADNI cohort" *Neurobiology of Aging* 31:1401-1418 (2010).

Robbins et al. "Cambridge Neuropsychological Test Automated Battery (CANTAB): a factor analytic study of a large sample of normal elderly volunteers" *Dementia* 5(5):266-281 (1994) (Abstract only).

Samieri et al. "Plasma long-chain omega-3 fatty acids and atrophy of the medical temporal lobe" *Neurology* 79(7):642-650 (2012).

Scheltens et al. "Efficacy of Souvenaid in Mild Alzheimer's Disease: Results from a Randomized, Controlled Trial" *Journal of Alzheimer's Disease* 31:225-236 (2014).

Selley, Michael L. "A metabolic link between S-adenosylhomocysteine and polyunsaturated fatty acid metabolism in Alzheimer's disease" *Neurobiology of Aging* 28:1834-1839 (2007).

Seshadri et al. "Plasma Homocysteine as a Risk Factor for Dementia and Alzheimer's Disease" *The New England Journal of Medicine* 346(7):476-483 (2002).

Shah et al. "The S-Connect study: results from a randomized, controlled trial of Souvenaid in mild-to-moderate Alzheimer's disease" *Alzheimer's Research & Therapy* 5(59):1-9 (2013).

Smith, A. David "Imaging the progression of Alzheimer pathology through the brain" *Proceedings of the National Academy of Sciences USA* 99(7):4135-4137 (2002).

Smith, A. David "The worldwide challenge of the dementias: A role for B vitamins and homocysteine?" *Food and Nutrition Bulletin* 29(2):S143-S172 (2008).

Smith et al. "Homocysteine-Lowering by B Vitamins Slows the Rate of Accelerated Brain Atrophy in Mild Cognitive Impairment: A Randomized Controlled Trial" *PLoS One* 5(9):e12244 (2010).

Sydenham et al. "Omega 3 fatty acid for the prevention of cognitive decline and dementia (Review)" *Cochrane Database of Systematic Reviews* 6(CD005379):1-42 (2012).

Tan et al. "Red blood cell omega-3 fatty acid levels and markers of accelerated brain aging" *Neurology* 78(9):658-664 (2012).

Virtanen et al. "Circulating Omega-3 Polyunsaturated Fatty Acids and Subclinical Brain Abnormalities on MRI in Older Adults: The Cardiovascular Health Study" *Journal of the American Heart Association* 2(5):e000305 (2013).

(56) References Cited

OTHER PUBLICATIONS

Vogiatzoglou et al. "Vitamin $B_{12}$ status and rate of brain volume loss in community—dwelling elderly" *Neurology* 71(11):826-832 (2008).

Witte et al. "Long-Chain Omega-3 Fatty Acids Improve Brain Function and Structure in Older Adults" *Cerebral Cortex* 24(11):3059-3068 (2014).

Search Report corresponding to British Application No. GB1405033.0 dated Oct. 20, 2014.

Andreeva et al. Cognitive Function after supplementation with B vitamins and long-chain omega-3 fatty acids: ancillary findings from the SU.FOL.OM3 randomized trial[1-3ω], *Am. J. Clin Nutr* 94:278-286 (2011).

Bowman et al. "Nutrient biomarker patterns, cognitive function, and MRI measures of brain aging", *Neurology* 78:241-249 (2012).

Holford "The Prevention of Memory Loss and Progression to Alzheimer's Disease with B Vitamins. Antioxidants and Essential Fatty Acids: A Review of the Evidence", *JOM* 26(2):53-58 (2011).

Koivisto et al. "Special lipid-based diets alleviate cognitive deficits in the APPSwe/PS1dE9 transgenic mouse model of Alzheimer's disease independent of brain amyloid deposition", *Journal of Nutritional Biochemistry* 25:157-169 (2014).

Lopes da Silva et al. "Plasma nutrient status of Alzheimer's disease patients compared to cognitive intact elderly controls: a systematic review and meta-analysis", *European Journal of Neurology* 19(Suppl. 1);469 (2012).

Scheltens et al."Efficacy of a medical food in mild Alzheimer's disease: A randomized, controlled trial", *Alzheimer's & Dementia* 6:1-10 (2010).

Notification of Transmittal of the International Search Report and the Written Opinion of the International Searching Authority, or the Declaration corresponding to International Application No. PCT/GB2015/050786 mailed Aug. 24, 2015.

Genziani, Mirella, et al., "Subjective memory impairment, objective cognitive functioning and social activity in French older people: Findings from the 3C study", Geriatr. Gerontol. Int., 13(1):139-45 (2013).

Williams, Jonathan H., et al., "Minimal hippocampal width relates to plasma homocysteine in community-dwelling older people", Age and Ageing, 31:440-444 (2002).

\* cited by examiner

COMBINATION THERAPY COMPRISING AN OMEGA-3 FATTY ACID, A FOLATE SPECIES AND A VITAMIN B12 SPECIES

STATEMENT OF PRIORITY

This application is a continuation application of U.S. patent application Ser. No. 15/763,654, which is a 35 U.S.C. § 371 national phase application of International Application Serial No. International App. No.: PCT/GB2016/053058, filed Sep. 30, 2016, which claims the benefit, under 35 U.S.C. § 119 (a) of Great Britain Application No. 1517275.2, filed Sep. 30, 2015, the entire contents of each of which are incorporated by reference herein.

FIELD

The present invention provides a combined therapy comprising the use of one or more omega-3 fatty acids and one or more B vitamins and for treating cognitive impairment by slowing its progression, such cognitive impairment disorders include, especially but not exclusively, Mild Cognitive Impairment (MCI) and Alzheimer's disease (AD). The present invention also provides a treatment for individuals suffering from cognitive impairment disorders that occur as a result of brain or cerebral atrophy, the invention includes inter alia methods of treating and/or reducing progression of brain atrophy and pharmaceutical compositions or dietary supplements therefor.

BACKGROUND

In the cognitively healthy elderly, the brain shows significant progressive atrophy, brain atrophy is commonly associated with the process of normal ageing. However, in subjects with Mild cognitive impairment (MCI) (which is a syndrome characterized by a subtle decline in cognitive function, and is considered to be a transitory state between normal ageing and clinical dementia and Alzheimer's disease (AD)), dementia, or AD, the brain atrophy rates are markedly increased compared to cognitively healthy controls. In MCI, the rate of atrophy is generally higher in the subgroup that eventually converts to AD (Risacher et al Curr Alzheimer Res 2009; 6 (4): 347-61). As there are no available cures for AD, an alternative approach is strategies to delay disease progression at an early stage. Efficient interventions may be detected by a slowing of brain atrophy rate.

The role of omega-3 fatty acids in cognitive decline and dementia is a matter of some controversy and remains highly speculative. Epidemiological evidence suggests protective roles of dietary intake of omega-3 rich fish-oils, eicosapentaenoic acid (EPA), and docosahexaenoic acid (DHA) (Huang et al JAD 2010; 21 (3): 673-90). Case-control studies have revealed associations between DHA or EPA and brain volume and better white matter grade (Tan et al Neurobiology 2012; 78 (9): 658-64, Virtanen et al J Am Heart Assoc 2013; 2 (5): e000305). A recent study showed that daily fish-oil supplementation (880 mg DHA and 1320 mg EPA) in healthy elderly during 26 weeks prevented the loss of total grey matter volume (Witte et al Cereb Cortex 2013doi10.1093/cercor/bht163). In prospective studies, red blood cell DHA and EPA concentrations were positively correlated with higher total brain and hippocampal volumes eight years later (Pottala et al Neurology 2014 doi10.1212), and higher relative concentrations of plasma EPA was associated with a reduced brain atrophy rate in the medial temporal lobe (Samieri et al. Neurology 2012; 79 (7): 642-50). However, results from randomized clinical trials including omega-3 supplementation are not equally convincing ((Huang et al JAD 2010; 21 (3): 673-90, Sydenham et al Cochrane Database Syst Rev 2012; (6): CD005379). Indeed, Quinn et al JAMA; 2010 Nov. 3; 304 (17): 1903-11, concluded in a study of AD patients receiving DHA supplementation that, as compared to the placebo group, there was no effect on the rate of progression of cognitive and functional decline.

Homocysteine is a non-essential, sulfur-containing amino acid synthesized endogenously from methionine. Raised plasma total homocysteine (tHcy) is a recognized modifiable risk factor for cognitive impairment, dementia, and AD (Seshadri et al N Engl J med 2002; 365 (7): 476-83, Ravaglia et al Am J Clin Nutr 2005; 82 (3): 636-43). The plasma tHcy concentration is primarily determined by the B-vitamin status, i.e. folate, vitamins $B_6$, and $B_{12}$, which themselves are inversely associated with cognitive decline, brain atrophy and AD (Smith et al Food Nutr Bull 2008; 29 (Suppl 2) S143-72). Results from Vitacog®, a randomized clinical trial with homocysteine-lowering B vitamins in older people with MCI, showed that treatment with high dose folic acid and vitamins $B_6$ and $B_{12}$ markedly reduced the global brain atrophy rate, as well as atrophy rates in those grey matter regions most commonly associated with AD (Douaud et al Proc Natl Acad Sci USA 2013 doi 10.1073/pnas.1301816110, Smith et al PLOS one 2010; 5 (9) e12244 doi101371/journal. pone 0012244).

It is desirable for patients and clinicians alike, to provide treatments for delaying AD progression and progression of other cognitive impairment disorders at an early stage or to prevent such disorders developing in individuals at risk therefrom.

It is also desirable for patients and clinicians alike, to provide treatments for delaying progression and/or preventing brain atrophy in an individual or an individual at risk of developing brain atrophy.

BRIEF SUMMARY OF THE DISCLOSURE

According to a first aspect of the invention there is provided a composition comprising:
 (i) an omega-3 fatty acid or a derivative thereof;
 (ii) a folate species; and
 (iii) a vitamin $B_{12}$ species.
The composition may be for use in:
 a. reducing the rate of brain atrophy in a human subject;
 b. treating mild cognitive impairment (MCI) in a human subject;
 c. retarding the onset and/or development of MCI in a human subject;
 d. delaying or preventing the development of Alzheimer's disease in a human subject;
 e. reducing or retarding the rate of progression of, or retarding the onset of, AD in a human subject;
 f. treating age-associated memory impairment (AAMI) in a human subject;
 g. treating cognitive function in a human subject who suffers from or is at risk from MCI or AD;
 h. treating memory in an aging human subject;
 i. treating attention in an aging human subject;
 j. treating age-related cognitive decline in a human subject;
 k. maintaining or improving or delaying the rate of loss of cognitive function in an aging human subject;

l. reducing or delaying the rate of decline or maintaining the level of cognitive function in a human subject with age-related cognitive impairment or at risk thereof; and/or m. maintaining or improving or delaying the decline in ability to carry out activities of daily living associated with cognitive decline.

It will be appreciated that the composition may be for use in the treatment of individuals that are already presenting with the symptoms of the disease or condition or for individuals at risk of developing the disease or condition or for maintaining the status quo of symptoms or for the prophylaxis of the disease or condition.

The compositions of the invention maybe dietary or nutritional supplements.

Cerebral or brain atrophy can be as a result of a neurological condition, injury or a disease for example and without limitation such conditions include, epilepsy, traumatic brain injuries, strokes, Alzheimer's disease, multiple sclerosis, cerebral palsy, Huntington's disease, chronic wasting (cachexia) and AIDS patients who develop cachexia. Accordingly the use of the composition of the first aspect of the invention may preferably be used to treat the aforementioned conditions associated with cerebral atrophy.

Preferably, the omega-3 fatty acid may be, or comprise, DHA or EPA, or a combination thereof; more preferably the composition comprises both DHA and EPA.

The omega-3 fatty acid may be, or comprise, the free acid or a derivative of the omega-3 fatty acid, or a combination thereof. The derivative may be a pharmaceutically acceptable salt or an ester, or a combination thereof. The ester may be a glyceride, a phospholipid or an alkyl ester, for example an ethyl ester. The omega-3 fatty acid may be or comprise a combination of esters, for example a combination of mono-, di- and tri-glycerides. The omega-3 fatty acid may be or comprise a combination of the free acid and an ester thereof, e.g. a combination of the free acid and a plurality of esters thereof.

The omega-3 fatty acid, e.g. EPA and/or the DHA, may be, or comprise, the fatty acid in the form of a salt, therefore. Suitable salts include those formed with organic or inorganic bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, peridine, pyrrolidine, a mono-, di- or tri-lower alkylamine, for example ethyl-, tert-butyl-, diethyl-, diisopropyl-, triethyl-, tributyl- or dimethyl-propylamine, or a mono-, di or trihydroxy lower alkylamine, for example mono-, di- or triethanolamine.

The omega-3 fatty acid, e.g. EPA and/or DHA, may be, or comprise, the fatty acid in the form of an ester. Ester groups include those formed from the terminal carboxylic acid moiety of the omega-3 fatty acid and an alcohol, such as a $C_{1-12}$ alkyl ester, formed by reaction of the omega-3 fatty acid with an alcohol having from 1 to 12 carbons, preferably a $C_{1-6}$ alkyl ester formed by reaction of themegai-3 fatty acid with an alcohol having from 1 to 6 carbons, for example a methyl, ethyl, n-propyl, isopropyl, butyl, pentyl, or hexyl ester, formed by reaction of the omega-3 fatty acid with methanol, ethanol, n-propanol, iso-propanol, butanol, pentanol or hexanol. The ester may be, or comprise, an ethyl ester or a methyl ester, particularly an ethyl ester. The ester may be, or comprise, a glyceride, e.g. a mono-, di- and/or tri-glyceride. The ester may be, or comprise, a phospholipid, for example the phospholipid may be or comprise phosphatidylcholine, phosphatidylethanolamine, phosphatidylinositol, phosphatidylserine, ysophosphatidylcholine or sphingomyelin, or a combination thereof.

In one embodiment the composition comprises EPA and/or DHA. The EPA comprises, or is, EPA free acid and/or EPA ester, and the DHA comprises, or is, DHA free acid and/or DHA ester. The ester may in particular be a methyl ester or an ethyl ester. Alternatively, the ester may be another ester or ester combination disclosed herein. A combination of eicosapentaenoic acid and docosahexaenoic acid may be used (i.e. the free acids of EPA and DHA are used, rather than salts or esters).

The fatty acid amounts disclosed herein are calculated as the amount of free acid.

Omega-3 oils are essentially non-toxic and doses exceeding 20 grams per day have been taken over prolonged dosing periods without side effects. The WHO recommended daily dose (RDA) of both DHA and EPA is 300-500 mg. The maximum tolerated dose (MTD) of combined EPA and DHA is estimated as 21 g per day (Burns et al Clin Cancer Res; 1999; 5:3942-47). Dosages of DHA and EPA that have been recommended to treat various conditions are, for example: 1.1 g DHA and 1.6 g EPA for infant allergies; 1.8-2.2 g DHA and 2.7-3.2 g EPA for asthma; 3.4 g DHA and 6.2 g EPA for bipolar disease; 3.6 g DHA and 4.1 g EPA for cancer; more than 3.0 g combined DHA and EPA for cardiovascular disease; and between 2.0 to 4.0 g combined DHA and EPA for hypertriclyceridemia.

The total omega-3 fatty acid daily dosage in the use of the compositions may be from 0.4 g to 15 g. Preferably, the total omega-3 fatty acid daily dosage in the use of the compositions described herein is from 0.6 g to 15 g; thus, for combined DHA and EPA the daily dosage is suitably from 0.6 g to 15 g, i.e. an amount between the WHO RDA for each omega-3 fatty acid and 75% of the MTD of combined DHA and EPA and any value therebetween. The total omega-3 fatty acid daily dosage may be from 0.6 g to 15 g, e.g. 0.6 g to 10 g, and optionally 1 g to 10 g or 1 g to 5 g, e.g. 2 g to 5 g. The composition may comprise a daily dosage as mentioned in this paragraph.

DHA may be in an amount of from 0.2 to 15 g and any integer therebetween. For example DHA may be present at 0.2 g, with 0.001 or less to 0.05 g or more, incremental increases up to 10.0 g thereby encompassing an amount of, as an arbitrary example, 1.367 g.

DHA may be in amount of from 0.2 g to 5 g, e.g. 0.3 g to 5 g or 1 g to 5 g.

EPA may be in an amount of from 0.2 to 15 g or any integer therebetween. For example DHA may be present at 0.2 g with 0.001 or less to 0.05 g or more incremental increases to 10 g thereby encompassing an amount of, as an arbitrary example, 3.452 g.

EPA may be in amount of from 0.2 g to 5 g, e.g. 0.3 g to 5 g or 1 g to 5 g.

The vitamins mentioned in this specification, namely folate species, vitamin B6 and vitamin B12, may be in free form or may be as a salt thereof.

Folates are a family of compounds that exert similar vitamin activities. The members of the family may conveniently be referred to as "folate species". The simplest structural form of the vitamin is folic acid (pteroylmonoglutamate), which does not occur in vivo in nature but may be formed from other folate species; it is chemically stable under normal processing conditions and is absorbed and converted to active forms of folate in vivo. Natural food folates differ from folic acid in one or more of three ways: they may exist in a reduced state as dihydrofolate (DHF) or tetrahydrofolate (THF); methyl or other groups may be attached to the pteridine ring and the N-5 or N-10 position; and a polyglutamate side chain may be attached to the benzene ring. The folate species may therefore be, or comprise, any member of the folate family, and for example may be selected from:
a. folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one-carbon units at various levels of oxidation, or a combination of two or more thereof; or
b. dihydrofolate, tetrahydrofolate, [6S]-5-methyltetrahydrofolate, DL-5-methyl-5,6,7,8-tetrahydropteroyl-L-monoglutamic acid, 5,10-methylenetetrahydrofolate, 5,10-methenyl-tetrahydrofolate, 5,10-formimino-tetrahydrofolate, 5-formyltetrahydrofolate (leucovorin) and 10-formyltetrahydrofolate.

The folate species is preferably folic acid. An alternative preferred species is a folic acid salt, or a combination of salts. A combination of folic acid and its salts may be administered.

The folate species may be in an amount of between 0.1 mg to 10 mg and includes any value therebetween. For example 0.1 mg, 0.2 mg, 0.3 mg, 0.4 mg; 0.5 mg, 0.6 mg, 0.7 mg, 0.8 mg, 0.9 mg, 1.0 mg, 1.1 mg, 1.2 mg, 1.3 mg, 1.4 mg; 1.5 mg, 1.6 mg, 1.7 mg, 1.8 mg, 1.9 mg, 2.0 mg, 2.1 mg, 2.2 mg, 2.3 mg, 2.4 mg; 2.5 mg, 2.6 mg, 2.7 mg, 2.8 mg, 2.9 mg, 3.0 mg, 3.1 mg, 3.2 mg, 3.3 mg, 3.4 mg; 3.5 mg, 3.6 mg, 3.7 mg, 3.8 mg, 3.9 mg, 4.0 mg, 4.1 mg, 4.2 mg, 4.3 mg, 4.4 mg; 4.5 mg, 4.6 mg, 4.7 mg, 4.8 mg, 4.9 mg, 5.0 mg, 5.1 mg, 5.2 mg, 5.3 mg, 5.4 mg; 5.5 mg, 5.6 mg, 5.7 mg, 5.8 mg, 5.9 mg, 6.0 mg, 6.1 mg, 6.2 mg, 6.3 mg, 6.4 mg; 6.5 mg, 6.6 mg, 6.7 mg, 6.8 mg, 6.9 mg, 7.0 mg, 7.1 mg, 7.2 mg, 7.3 mg, 7.4 mg; 7.5 mg, 7.6 mg, 7.7 mg, 7.8 mg, 7.9 mg, 8.0 mg, 8.1 mg, 8.2 mg, 8.3 mg, 8.4 mg; 8.5 mg, 8.6 mg, 8.7 mg, 8.8 mg, 8.9 mg, 9.0 mg, 9.1 mg, 9.2 mg, 9.3 mg, 9.4 mg; 9.5 mg, 9.6 mg, 9.7 mg, 9.8 mg, 9.9 mg and 10.0 mg.

Preferably, the folate species, in particular folic acid, is in an amount of 0.5 mg to 1.5 mg e.g. an amount of 0.8 mg.

The vitamin $B_{12}$ species (also referred to herein as "the B12 vitamin") may be selected from:
a. cobalamin, cyanocobalamin, methylcobalamin, adenosylcobalamin in the form of a salt or free acid; or hydroxocobalamin and
b. vitamin $B_{12}$ as cyanocobalamin in the form of a salt or free acid.

Preferably the $B_{12}$ vitamin is in an amount of 0.01 mg to 2.00 mg or any value therebetween. For example 0.01 mg, 0.02 mg, 0.03 mg, 0.04 mg, 0.05 mg, 0.06 mg, 0.07 mg, 0.08 mg, 0.09 mg, 0.11 mg, 0.12 mg, 0.13 mg, 0.14 mg, 0.15 mg, 0.16 mg, 0.17 mg, 0.18 mg, 0.19 mg, 0.20 mg, 0.21 mg, 0.22 mg, 0.23 mg, 0.24 mg, 0.24 mg, 0.25 mg, 0.26 mg, 0.27 mg, 0.28 mg, 0.29 mg, 0.30 mg, 0.31 mg, 0.32 mg, 0.33 mg, 0.34 mg, 0.35 mg, 0.36 mg, 0.37 mg, 0.38 mg, 0.39 mg, 0.40 mg, 0.41 mg, 0.42 mg, 0.43 mg, 0.44 mg, 0.45 mg, 0.46 mg, 0.47 mg, 0.48 mg, 0.49 mg, 0.50 mg, 0.51 mg, 0.52 mg, 0.53 mg, 0.54 mg, 0.54 mg, 0.55 mg, 0.56 mg, 0.57 mg, 0.58 mg, 0.59 mg, 0.60 mg, 0.61 mg, 0.62 mg, 0.63 mg, 0.64 mg, 0.65 mg, 0.66 mg, 0.67 mg, 0.68 mg, 0.69 mg, 0.70 mg, 0.71 mg, 0.72 mg, 0.73 mg, 0.74 mg, 0.75 mg, 0.76 mg, 0.77 mg, 0.78 mg, 0.79 mg, 0.80 mg, 0.81 mg, 0.82 mg, 0.83 mg, 0.84 mg, 0.85 mg, 0.86 mg, 0.87 mg, 0.88 mg, 0.89 mg, 0.90 mg, 0.91 mg, 0.92 mg, 0.93 mg, 0.94 mg, 0.95 mg, 0.96 mg, 0.97 mg, 0.98 mg, 0.99 mg, 1.00 mg, 1.01 mg, 1.02 mg, 1.03 mg, 1.04 mg, 1.05 mg, 1.06 mg, 1.07 mg, 1.08 mg, 1.09 mg, 1.20 mg, 1.21 mg, 1.22 mg, 1.23 mg, 1.24 mg, 1.24 mg, 1.25 mg, 1.26 mg, 1.27 mg, 1.28 mg, 1.29 mg, 1.30 mg, 1.31 mg, 1.32 mg, 1.33 mg, 1.34 mg, 1.35 mg, 1.36 mg, 1.37 mg, 1.38 mg, 1.39 mg, 1.40 mg, 1.41 mg, 1.42 mg, 1.43 mg, 1.44 mg, 1.45 mg, 1.46 mg, 1.47 mg, 1.48 mg, 1.49 mg, 1.50 mg, 1.51 mg, 1.52 mg, 1.53 mg, 1.54 mg, 1.55 mg, 1.56 mg, 1.57 mg, 1.58 mg, 1.59 mg, 1.60 mg, 1.61 mg, 1.62 mg, 1.63 mg, 1.64 mg, 1.65 mg, 1.66 mg, 1.67 mg, 1.68 mg, 1.69 mg, 1.70 mg, 1.71 mg, 1.72 mg, 1.73 mg, 1.74 mg, 1.75 mg, 1.76 mg, 1.77 mg, 1.78 mg, 1.79 mg, 1.80 mg, 1.81 mg, 1.82 mg, 1.83 mg, 1.84 mg, 1.85 mg, 1.86 mg, 1.87 mg, 1.88 mg, 1.89 mg, 1.90 mg, 1.91 mg, 1.92 mg, 1.93 mg, 1.94 mg, 1.95 mg, 1.96 mg, 1.97 mg, 1.98 mg, 1.99 mg and 2.00 mg.

Preferably, the $B_{12}$ vitamin, in particular cyanocobalamin, is in an amount of between 0.4 mg to 1 mg, in particular 0.5 mg.

Preferably, the composition further includes at least one or more B vitamin in addition to the $B_{12}$ vitamin, more preferably the additional B vitamin is a vitamin $B_6$ species, either in the form of a salt or free acid.

Preferably, the vitamin $B_6$ species is in an amount of 1 mg to 40 mg or any value therebetween. For example 1 mg, 2 mg, 3, mg, 4 mg, 5 mg, 6 mg, 7 mg, 8 mg, 9 mg, 10 mg, 11 mg, 12 mg, 13, mg, 14 mg, 15 mg, 16 mg, 17 mg, 18 mg, 19 mg, 20 mg, 21 mg, 22 mg, 23, mg, 24 mg, 25 mg, 26 mg, 27 mg, 28 mg, 29 mg, 30 mg, 31 mg, 32 mg, 33, mg, 34 mg, 35 mg, 36 mg, 37 mg, 38 mg, 39 mg and 40 mg or any value of 0.1 to 0.9 mg therebetween.

Vitamin $B_6$ has three naturally occurring forms: pyridoxal, pyridoxine and pyridoxamine. It is commonly administered as pyridoxine hydrochloride. The terms "vitamin $B_6$" and "vitamin B6 species" herein refer to any substance having the activity of vitamin B6, e.g. pyridoxine hydrochloride. Preferably, the vitamin B6 or derivative thereof is in an amount of 15 mg to 30 mg, in particular 20 mg.

The term "vitamin B12" refers to a vitamin B12 species, in particular cyanocobalamin, and the term "vitamin B6" refers to a vitamin B6 species, in particular pyridoxine hydrochloride. The vitamin B6 species and the vitamin B12 species may be as a free acid or a salt thereof.

Preferably, the composition comprises the following agents as a salt or free acid or derivative thereof:
(i) an omega-3 fatty acid;
(ii) a folate species;
(iii) vitamin $B_{12}$; and
(iv) vitamin $B_6$.

Preferably, the composition comprises:
(i) DHA in an amount of from 0.2 to 5 g;
(ii) EPA in an amount of from 0.2 to 5 g.
(iii) a folate species in an amount of from 0.1 mg to 10 mg;
(iv) vitamin $B_{12}$ in an amount of from 0.01 mg to 2 mg; and
(v) vitamin $B_6$, is in an amount of from 15 mg to 30 mg.

Preferably, the composition comprises:
(i) DHA in an amount of from 0.3 to 5 g;
(ii) EPA in an amount of from 0.3 to 5 g;
(iii) a folate species in an amount of 0.8 mg;
(iv) vitamin $B_{12}$ in an amount of 0.5 mg; and
(v) vitamin $B_6$, is in an amount of 20 mg.

Preferably, the composition is for use in a human subject who is at least 50 years old, this encompasses any subject over the age of 50 e.g. is at least 60 or 70 years old and beyond. In this respect "aging" human subject is intended to refer to individuals over 50 years of age.

Preferably, the composition is for oral administration.

Preferably, the medicament is for use in treating a disorder as listed hereinbefore as a-m.

Preferably, the composition is a dietary or food supplement, a nutritional supplement or a medical food for use in treating a disorder as listed hereinbefore as a-m.

Preferably, the human subject has a baseline homocysteine level above about 9.5 µmol/L.

Preferably, the compositions further include betaine and/or choline in a dosage form which comprises approximately from 1 g to 6 g of said choline or betaine e.g. 1, 2, 3, 4, 5 or 6 g.

The compositions of the present invention provide a plurality of agents which lowers homocysteine (tHcy) levels for use in the treatment of cognitive disorders.

In a second aspect of the invention, the compositions as hereinbefore described may all be used for the manufacture of a medicament or nutritional supplement for the treatment of conditions listed hereinbefore as (a-m).

Also included in the present invention is the use of a plurality of agents which lowers homocysteine (tHcy) levels in the manufacture of a medicament for the treatment of cognitive disorders in a subject.

The compositions, supplements and/or medicaments of the present invention may be for use to (a) improve mental vitality; (b) improve executive function; (c) improve reaction time; (d) slow progressive atrophy of the brain and/or (e) improve learning or memory in the subject.

According to a third aspect of the invention there is provided a pharmaceutical composition or nutritional supplement selected from:
a. compositions consisting of a pharmaceutically acceptable carrier and the following agents:
(i) an omega-3 fatty acid selected from DHA and EPA or a derivative thereof or a combination thereof the omega-3 fatty acid being in amount of between 0.6 to 15 g;
(ii) a folate species in an amount of 0.5 mg to 1.5 mg;
(iii) vitamin $B_6$ or a derivative thereof in an amount of 15 mg to 30 mg;
(iv) vitamin $B_{12}$ or a derivative thereof in an amount of 0.4 mg to 1.0 mg; and
b. compositions comprising a pharmaceutically acceptable carrier and the following agents in the form of a salt or free acid:
i. 0.6 to 15 g of an omega-3 fatty acid selected from DHA and EPA or a combination thereof;
ii. 0.1 mg to 10 mg of a folate species; and
iii. 0.01 mg to 2 mg of vitamin $B_{12}$ or a derivative thereof, optionally wherein the composition is selected from the compositions (a) wherein:
the folate species is in an amount of 0.8 mg;
the vitamin $B_6$ of derivative thereof is in an amount of 20 mg; and
the vitamin $B_{12}$ or derivative thereof is in an amount of 0.5 mg.

The folate species, the vitamin B6 and the vitamin B12 may be in free form or as a salt thereof, or as a combination thereof.

According to a fourth aspect of the invention there is provided a composition according to the first aspect of the invention or the medicament or supplement according to the second aspect of the invention or the pharmaceutical composition or supplement according to the third aspect of the invention for use in treating any one or more of the following conditions in a human:
a. reducing the rate of brain atrophy in a human subject;
b. treating mild cognitive impairment (MCI) in a human subject;
c. retarding the onset and/or development of MCI in a human subject;
d. delaying or preventing the development of Alzheimer's disease in a human subject;
e. reducing or retarding the rate of progression of, or retarding the onset of, AD in a human subject;
f. treating age-associated memory impairment (AAMI) in a human subject;
g. treating cognitive function in a human subject who suffers from or is at risk from MCI or AD;
h. treating memory in an aging human subject;
i. treating attention in an aging human subject;
j. treating age-related cognitive decline in a human subject;
k. maintaining or improving or delaying the rate of loss of cognitive function in an aging human subject;
l. reducing or delaying the rate of decline or maintaining the level of cognitive function in a human subject with age-related cognitive impairment or at risk thereof; and
m. maintaining or improving or delaying the decline in ability to carry out activities of daily living associated with cognitive decline,
wherein the human has an average or a reduced circulating plasma level of DHA and/or EPA as compared to average normal circulating levels of DHA and EPA. The human may have a total plasma level of DHA below about 270 µM, in particular below about 250 µM. The human may have a total plasma level of EPA below about 150 µM, in particular below about 140 µM. The human may have a total plasma level of DHA below about 270 µM and a total plasma level of EPA below about 150 µM. The human may have a total plasma level of DHA below about 250 µM and a total plasma level of EPA below about 140 µM.

The average total plasma level of DHA is in the range of 268-310 µM (95% confidence limit of geometric mean in Vitacog® study). It will be appreciated from the literature that there are numerous ways to measure fatty acids, in the present invention the total plasma concentration is used by which it is meant the total concentration of a certain fatty acid in all plasma lipid fractions combined. Individuals having a total plasma level of DHA below about 250 µM are considered to have a low DHA level, whereas individuals having a plasma DHA level of above about 340 µM are considered to have high DHA levels.

The average total plasma level of EPA is in the range 161-200 µM. Individuals having a plasma level of EPA below about 140 µM are considered to have a low EPA level, whereas individuals having a plasma EPA level of above about 220 µM are considered to have high EPA levels.

Preferably, the invention of the fourth aspect of the invention is intended to treat cognitive impairment conditions in individuals having an average or below plasma level of the mean average for DHA and EPA. It is also preferable that the individuals that would benefit from the method of the fourth aspect of the invention have a low total homocysteine level.

Preferably, the human subject has a baseline homocysteine level above about 9.5 µmol/L.

According to a further aspect of the invention there is provided a method of reducing the rate of brain atrophy in a human subject in a human subject, comprising administering the composition according to the first aspect of the invention or the medicament according to the second aspect of the invention or the pharmaceutical composition according to the third aspect of the invention.

Cerebral atrophy can be as a result of a neurological condition, injury or a disease for example and without limitation such conditions include, epilepsy, traumatic brain injuries, strokes, Alzheimer's disease, multiple sclerosis, cerebral palsy, Huntington's disease, chronic wasting (cachexia) and AIDS patients who develop cachexia. The method of the present invention may therefore preferably be used to treat brain atrophy associated with any of these conditions.

According to a further aspect of the invention there is provided a method of treating mild cognitive impairment (MCI) in a human subject, comprising administering the composition according to the first aspect of the invention or the medicament according to the second aspect of the invention or the pharmaceutical composition according to the third aspect of the invention.

According to a further aspect of the invention there is provided a method of retarding the onset and/or development of MCI in a human subject, comprising administering the composition according to the first aspect of the invention or the medicament according to the second aspect of the invention or the pharmaceutical composition according to the third aspect of the invention.

According to a further aspect of the invention there is provided a method of delaying or preventing the development of, or retarding the onset of, AD in a human subject, comprising administering the composition according to the first aspect of the invention or the medicament according to the second aspect of the invention or the pharmaceutical composition according to the third aspect of the invention.

According to a further aspect of the invention there is provided a method of reducing or retarding the rate of progression of AD in a human subject, comprising administering the composition according to the first aspect of the invention or the medicament according to the second aspect of the invention or the pharmaceutical composition according to the third aspect of the invention.

According to a further aspect of the invention there is provided a method of treating age-associated memory impairment (AAMI) in a human subject, comprising administering the composition according to the first aspect of the invention or the medicament according to the second aspect of the invention or the pharmaceutical composition according to the third aspect of the invention.

According to a further aspect of the invention there is provided a method of treating cognitive function in a human subject who suffers from or is at risk from MCI or AD in a human subject, comprising administering the composition according to the first aspect of the invention or the medicament according to the second aspect of the invention or the pharmaceutical composition according to the third aspect of the invention.

According to a further aspect of the invention there is provided a method of treating memory loss in an aging human subject, comprising administering the composition according to the first aspect of the invention or the medicament according to the second aspect of the invention or the pharmaceutical composition according to the third aspect of the invention.

According to a further aspect of the invention there is provided a method of treating attention in a human subject in an aging human subject in a human subject, comprising administering the composition according to the first aspect of the invention or the medicament according to the second aspect of the invention or the pharmaceutical composition according to the third aspect of the invention.

According to a further aspect of the invention there is provided a method of treating age-related cognitive decline in a human subject, comprising administering the composition according to the first aspect of the invention or the medicament according to the second aspect of the invention or the pharmaceutical composition according to the third aspect of the invention.

According to a further aspect of the invention there is provided a method of maintaining or improving cognitive function or reducing the rate of loss of cognitive function in an aging human subject, comprising administering the composition according to the first aspect of the invention or the medicament according to the second aspect of the invention or the pharmaceutical composition according to the third aspect of the invention.

According to a further aspect of the invention there is provided a method of reducing or delaying the rate of decline or maintaining the level of cognitive function in a human subject with age-related cognitive decline, comprising administering the composition according to the first aspect of the invention or the medicament according to the second aspect of the invention or the pharmaceutical composition according to the third aspect of the invention.

According to a further aspect of the invention there is provided a method of maintaining or improving or delaying the decline in ability to carry out activities in daily living associated with cognitive decline, comprising administering the composition according to the first aspect of the invention or the medicament according to the second aspect of the invention or the pharmaceutical composition according to the third aspect of the invention.

According to a further aspect of the invention there is provided a method of reducing the rate of brain atrophy and decline of cognitive function in a human subject having reduced circulating plasma levels of DHA and EPA, comprising administering the composition according to the first aspect of the invention or the medicament according to the second aspect of the invention or the pharmaceutical composition according to the third aspect of the invention.

Embodiments of the methods described herein may result in the improvement or maintenance of mental capability in the subject following administration of the compositions of the present invention. Alternatively, or in addition, executive function and/or reaction time and/or learning or memory may be improved or maintained in the subject following administration of compositions of the present invention. The administration may be over a period of days, weeks, months or years.

In one embodiment, the method(s) of the invention comprise the simultaneous, separate or sequential administration of the omega-3 fatty acid, folic acid, $B_6$ and $B_{12}$ vitamins.

Further provided is a method for:
a. reducing the rate of brain atrophy in a human subject;
b. treating mild cognitive impairment (MCI) in a human subject;
c. retarding the onset and/or development of MCI in a human subject;
d. delaying or preventing the development of Alzheimer's disease in a human subject;
e. reducing or retarding the rate of progression of, or retarding the onset of, AD in a human subject;
f. treating age-associated memory impairment (AAMI) in a human subject;

g. treating cognitive function in a human subject who suffers from or is at risk from MCI or AD;

h. treating memory in an aging human subject;

i. treating attention in an aging human subject;

j. treating age-related cognitive decline in a human subject;

k. maintaining or improving or delaying the rate of loss of cognitive function in an aging human subject;

l. reducing or delaying the rate of decline or maintaining the level of cognitive function in a human subject with age-related cognitive impairment or at risk thereof; and/or m. in a human subject, maintaining or improving or delaying the decline in ability to carry out activities of daily living associated with cognitive decline, the method comprising administering to the human subject the following agents:

(i) an omega-3 fatty acid or a derivative thereof;

(ii) a folate species; and (iii) vitamin $B_{12}$ or a derivative thereof, either in the form of a salts or free acids.

The agents may be administered simultaneously, separately or sequentially. Any two or more of the agents may be administered in a fixed combination, e.g. in a tablet or capsule. The agents, or any two of them, may be administered in free combination, i.e. in separate dosage forms. For example, the vitamins (folate species, vitamin B6 species and vitamin B12 species) may be administered in a single composition and the omega-3 fatty acid species in a separate dosage form.

Preferably, the method comprises the following agents as a salt or free acid or derivative thereof:

(i) an omega-3 fatty acid;

(ii) a folate species;

(iii) vitamin $B_{12}$; and (iv) vitamin $B_6$.

Preferably, the method comprises administering:

(i) DHA in an amount of from 0.2 to 5 g;

(ii) EPA in an amount of from 0.2 to 5 g.

(iii) a folate species in an amount of from 0.1 mg to 10 mg;

(iv) vitamin $B_{12}$ in an amount of from 0.01 mg to 2 mg; and (v) vitamin $B_6$, is in an amount of from 15 mg to 30 mg.

Preferably, the method comprises administering:

(i) DHA in an amount of from 0.3 to 5 g;

(ii) EPA in an amount of from 0.3 to 5 g;

(iii) a folate species in an amount of 0.8 mg;

(iv) vitamin $B_{12}$ in an amount of 0.5 mg; and (v) vitamin $B_6$, is in an amount of 20 mg.

More particularly the agents and the dosages in which they are administered may be as described herein in relation to the compositions of the invention, although it will be appreciated that in this method of the invention the agents do not have to be administered together in a single composition, The amounts of the agents (e.g. DHA, EPA, folate species, vitamin B12, vitamin B6) mentioned herein may be administered per day in the methods of the invention.

The invention and this disclosure further include the subject matters of the claims.

It will be appreciated that any feature ascribed to one aspect of the invention applies equally to each and every other aspect of the invention mutatis mutandis.

BRIEF DESCRIPTION OF THE DRAWINGS

Embodiments of the invention are further described hereinafter with reference to the accompanying drawings, in which.

DEFINITIONS

Figure 1:
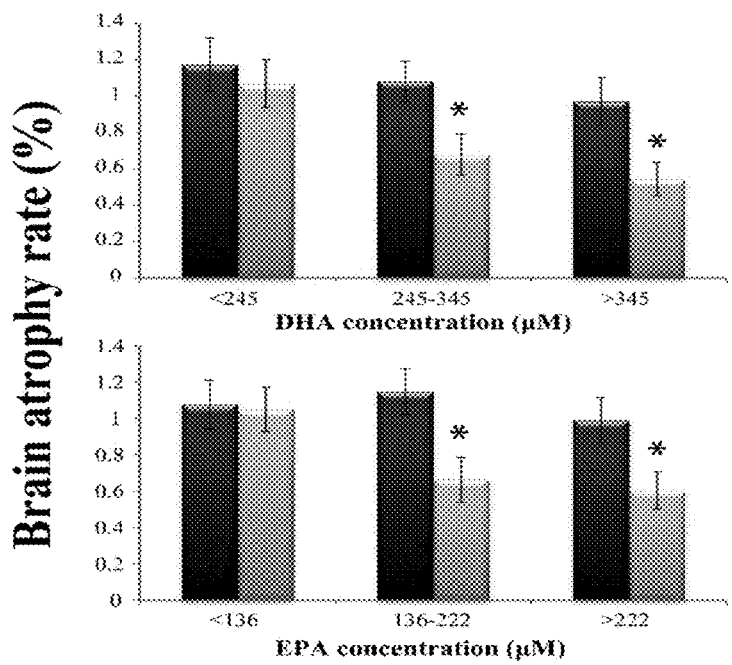
FIG. 1 shows the comparison of annual brain atrophy rate between placebo (black) and B vitamin treatment (gray) (+/−SEM) based on tertiles of baseline DHA (top) and EPA (bottom). An asterisk (*) indicates a significant difference between groups as assessed with independent t-tests (P<0.05).

As used herein, the term "brain atrophy" or cerebral atrophy, refers to any condition or circumstance in which tissue or cells in the brain are lost or damaged, or the connections between neurones or other brain cells are damaged. Cranial magnetic resonance imaging (MRI) is established as a method to monitor disease progression. Symptoms of cerebral atrophy can be generalized (affecting the whole brain) or localized (affecting only one part of the brain or one function). Generalized brain atrophy refers to a shrinkage of the entire brain. Physicians see this in aging patients as patients begin to lose neurons and brain cells, resulting in the reduced weight and size of the brain. In addition to the loss of neurons over time, neurons themselves can reduce in size and shrink, also resulting in cerebral atrophy. Generalized symptoms include symptoms of dementia, such as problems with memory or changes in personality. Localized symptoms include seizures and problems with speech, vision of movement. Cerebral atrophy can be as a result of a neurological condition, injury or a disease for example and without limitation such conditions include, epilepsy, traumatic brain injuries, strokes, Alzheimer's disease, multiple sclerosis, cerebral palsy, Huntington's disease, chronic wasting (cachexia) and AIDS patients who develop cachexia.

As used herein, the term "cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, executive function, the temporal integration of voluntary behaviour, and expressing an interest in one's surroundings and self-care. In one embodiment, the present invention results in improved memory. In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). See Folstein et al., J Psychiatric Res 12:189-98, (1975); Robbins et al., Dementia 5:266-81, (1994); Rey, L'examen clinique en psychologie, (1964); Kluger et al., J Geriatr Psychiatry Neurol 12:35168-79, (1999). In animal model systems, cognitive function may be measured in various conventional ways known in the art, including using a Morris Water Maze (MWM), Barnes circular maze, elevated radial arm maze, T maze or any other mazes in which the animals use spatial information. Other tests known in the art may also be used to assess cognitive function, such as novel object recognition and odour recognition tasks. Cognitive function may also be measured using imaging techniques such as Positron Emission Tomography (PET), functional magnetic resonance imaging (flvIRI), Single Photon Emission Computed Tomography (SPECT), or any other imaging technique that allows one to measure brain function. In animals, cognitive function may also be measured with electrophysiological techniques. Thus, in one embodiment, the present invention relates to the improvement of cognitive function of a subject. The subject may be an elderly subject e.g. over the age of 60, e.g. 70, 75 or 80 years of age.

As used herein, reference to "cognitive impairment" is intended to include any cognitive disorders that that involve a degree of brain atrophy, the brain atrophy may be a result of a clinical condition or may be the result of the natural aging process, injury or stroke. In this respect the treatments provided by the present invention may be for Mild Cognitive Impairment (MCI), a term given to a disorder which is typically characterised by a degree of cognitive impairment that does not affect daily life significantly. Other cognitive disorders that may be treatable by the compositions of the present invention include Alzheimer's Disease (AD), Age-Associate Memory Impairment (AAMI), Age Related Memory Loss (ARML), Age-Related Cognitive Decline (ARCD) and dementia whether it be pre-senile or otherwise. Treatments provided by the present invention also may be for brain atrophy that is the result of, for example, brain injury.

As used herein, the term "Mild Cognitive Impairment" or "MCI" relates to a disorder or condition in which individuals have cognitive impairment beyond that expected for their age and education but which typically does not interfere with their daily activities. In some embodiments, the term "MCI" relates to a condition which may be considered a boundary or transitional stage between normal aging and dementia. MCI can present with a variety of cognitive symptoms including, for example, memory loss. Memory loss may be confirmed by for example; (a) the subject's report of his or her own memory impairment, which may be confirmed by another person; and/or (b) measurable, greater-than-normal memory impairment detected with standard memory assessment tests (Petersen R C, Roberts R O, Knopman D S, Boeve B F, Geda Y E, et al. (2009) Mild cognitive impairment: ten years later. Arch Neurol 66:1447-1455). In one embodiment, the invention relates to the treatment or slowing of progression of MCI in a subject comprising the use of the compositions of the present invention. The combined omega-3 fatty acids and B vitamins for use in the present invention are described in more detail below. In one embodiment, the MCI may be amnestic MCI. In one embodiment, the subject does not suffer from other impairments of brain function, such as planning or attention. In an alternative embodiment, the subject has impairments of memory, language, or another mental function such that they suffer from (c) a decline in normal general thinking and reasoning skills and/or (d) a decline in a subject's ability to perform normal daily activities. Such impairments may be severe enough to be noticeable to other people and to show up on tests, but not serious enough to interfere with daily life. In one embodiment the individual is 50 years of age or greater e.g. 55, 60, 65, 70, 75, 80 or 85 years of age.

As used herein, "Age-Associate Memory Impairment (AAMI)" refers to a decline in memory due to aging. A patient or subject may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.). In one embodiment, the invention comprises the treatment of AAMI by the administration of the compositions as described herein.

As used herein, the terms "Age-Related Cognitive Decline (ARCD)" and "Age Related Memory Loss" (ARML), refers to declines in memory and cognitive abilities that are a normal consequence of aging in humans. This is also true in virtually all mammalian species. In one embodiment, the invention comprises treating or reducing the rate of ARCD/ARML by administering a composition as described herein.

As used herein, the terms "treatment" and "treating" an intervention in an attempt to alter the natural course of the individual being treated, and may be performed either for prophylaxis or for improvement. Treatment may be for stasis or stability of a condition. Desirable effects include helping to support or maintain function, preventing occurrence or recurrence or progression of disease, improvements, help to support, maintaining disease status, stabilizing disease status, prevention, prophylaxis, alleviation of symptoms, diminishment of any direct or indirect pathological consequences of the disease, elongation of asymptomatic disease phase, elongation of phase to on-set of disease, lowering the rate of disease progression, amelioration or palliation of the disease state, and remission or improved prognosis. A condition or subject refers to taking steps to obtain beneficial or desired results, including clinical results. Beneficial or desired clinical results include, but are not limited to, stasis, alleviation, reversal, maintenance, reduction in rate, maintenance, prevention, inhibition, retardation, delay of initiation or progression, or amelioration of one or more symptoms associated with brain atrophy, delay, retardation or slowing of that impairment, amelioration, palliation or stabilization of that impairment, and other beneficial results, such as improvement of cognitive function, brain memory function, mental and memory performance, mental agility and vitality, mental competence, mental aptitude, mental performance, brain memory function, promotion or improved concentration or a reduced rate of decline or retardation of cognitive function in subjects with age-related cognitive impairment or at risk thereof. Further beneficial results include but are not limited to improvements in brain memory function and reasoning. Reference herein to "treat" or "treatment" also includes a reduction in the rate of decline or retardation to the extent that it may be halted to a rate of zero, so that in a comparable untreated individual, the effect may be seen as an improvement.

As used herein, the terms "patient", "subject", or "individual" are used interchangeably and refer to either a human or a non-human animal. These terms include mammals, such as humans, primates, livestock animals (including bovines, caprines, ovines, porcines, etc.), companion animals (e.g., canines, felines, etc.) and rodents (e.g., mice and rats). In a preferred embodiment, the subject is a human.

A "therapeutically effective amount" of a drug or agent, e.g. the compositions of the present invention, is an amount of a drug or an agent that, when administered to a subject will have the intended therapeutic effect, e.g. slowing of brain atrophy or improving cognitive function in a subject, e.g., a patient with MCI or a patient at risk thereof, or a patient with AD or at risk thereof or any other condition associated with brain atrophy hereinbefore mentioned. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled worker can readily determine the effective amount for a given situation by routine experimentation. In one embodiment, the compositions as described herein are for administration on a daily frequency or more than once a day, e.g. 2, 3 or 4 times a day.

The term "supplement", "dietary supplement", "food supplement", "nutritional supplement" or "medical food" as used herein, refers to a composition which is consumed in addition to the daily meals or in between. A "dietary supplement" refers to a product that contains a "dietary ingredient" intended to supplement the diet. "Dietary ingredient" includes, but is not limited to the compositions of the present invention.

The term "fatty acid" as used herein refers to an omega-3-fatty acid that may be in free form, or it may be an ester, a pharmaceutically acceptable salt thereof, or a combination thereof. As an ester may be mentioned a monoglyceride, a diglycerides or a triglyceride, a phospholipid or an alkyl ester, or a combination thereof.

A "combined" therapy of the agents of the present invention is a therapy where the agents may be combined as a single dosage form or may be in multiple dosage forms and may be administered sequentially or simultaneously.

DETAILED DESCRIPTION

Only two reports investigating omega-3 fatty acids along with B vitamins have been reported in the context of cognitive performance. One of these investigated a nutritional supplement which among other nutrients included omega-3 fatty acids (EPA, 300 mg, and DHA 1200 mg) and B vitamins (folic acid, 0.4 mg, vitamin $B_6$, 1 mg, vitamin $B_{12}$, 0.003 mg) (Scheltens et al JAD 2012; 31 (1): 225-36). The supplement produced some beneficial effects in mild AD when given for 24 weeks, but this has not been confirmed in a larger follow-up study (Shah et al Alzheimer's Res Ther 2013; 5 (6): 59), which casts doubts on the initial findings. The second study used a 2×2 factorial design, with one B vitamin component (folate, 0.56 mg, vitamins $B_6$, 3 mg, and vitamin $B_{12}$, 0.02 mg) and one with omega-3 fatty acids (EPA, 400 mg, and DHA 200 mg), and found that this combination decreased the likelihood of a low score on temporal orientation task in a subgroup with prior stroke (Andreeva et al Am J clin Nutr 2011; 94 (1): 278-86). Both studies above were in populations with different characteristics and used much lower doses of B vitamins compared VITACOG, and none of these report brain volume or brain atrophy data.

The present invention provides the first evidence of the interaction of homocysteine and fatty acids on brain atrophy rate and it the first evidence of that plasma omega-3 fatty acid status modifies the response to high dose vitamin $B_{12}$, vitamin $B_6$, and folic acid supplementation on brain atrophy rates and on cognitive decline.

A randomized, placebo-controlled trial, was conducted and results showed the effect of high dose B vitamin supplementation on the brain atrophy rate or cognitive decline is augmented by a high baseline status of long-chain omega-3 fatty acids. B vitamin supplementation reduced the average brain atrophy rate in subjects with high plasma concentrations of DHA (>345 μM) or EPA (>222 μM) by approximately 40%, compared with subjects in the placebo group. Equally important, it was demonstrated that B vitamin supplementation has no effect on the rate of brain atrophy in subjects with low DHA (<245 μM) and EPA (<136 μM). It was also shown that the B vitamin supplementation had no effect on cognitive decline at low levels of the total of DHA and EPA (<390 μM) but that cognitive decline was prevented in those with high plasma concentrations (>590 μM) of the combined omega-3 fatty acids (DHA and EPA).

One major effect of the combined high dose B vitamin treatment is to lower plasma tHcy. In the VITACOG study, the tHcy concentration was reduced by 31.7% compared with placebo, and the treatment of subjects with baseline tHcy above 11.3 μM reduced the brain atrophy rate by 43% compared with the placebo group (Smith et al, PLOS One 2010; 5 (9); e12244.doi10.1371/journal.pone. 0012244). When further divided into tertiles of baseline plasma total DHA, we show that this difference between treatment groups was more pronounced in the moderate (245-345 μM) and high (>345 M) tertile, as the atrophy rates were reduced by 53.3% and 75.8%, respectively. In subjects with low baseline tHcy, no significant difference between the placebo and B vitamin groups, regardless of omega-3 status was found. Results indicate that the effect of B vitamins in subjects with moderate to high omega-3 concentrations is mainly driven by subjects with elevated levels of homocysteine at the start of the treatment. It is therefore hypothesized that a low homocysteine status facilitates the beneficial effect of omega-3 fatty acids. Other lines of evidence support this hypothesis. When dividing the entire group by tHcy at the end of the study, thus being able to investigate the entire study population and increase the power, increasing DHA and EPA concentrations at baseline were associated with decreased brain atrophy rates in subjects with low tHcy.

In conclusion, the present invention provides evidence that the effect of B vitamin supplementation on brain atrophy rates or cognitive decline depends upon pre-existing long-chain omega-3 fatty acid concentrations; this finding could possibly explain why previous some B vitamin trials on brain function have failed. Conversely, results suggest that tHcy status might be an important factor to consider when evaluating the effects of omega-3 fatty acid in cognitive decline and dementia, and so could explain why some trials of omega-3 fatty acids have failed. A negative correlation was found to exist between DHA/EPA concentrations and the brain atrophy rate. This association was stronger in the treated group, suggesting that omega-3 supplementation might be beneficial not only to those with "low" baseline levels.

Agents

The present invention relates to the use of a combination of agents which are capable of reducing the rate of brain atrophy in a subject in need thereof. The agents of the invention and methods which comprise the use of such agents may be for long term administration. That is to say, embodiments of the invention comprise administering the agents for a period of days, weeks, months or years. In one embodiment, the agents are for administration at least once a day for a month, 2, 3, 4, 5, 6, 7, 8, 9, 10, 11, 12, 13, 14, 15, 16, 17, 18, 19, 20, 21, 22, 23 or 24 months or more.

Omega-3 Fatty Acids

Omega-3 fatty acids are vital for normal metabolism but some of the potential health benefits of supplementation are controversial. Omega-3s are considered essential fatty acids. The three types of omega-3 fatty acids involved in human physiology are α-linolenic acid (ALA), eicosapentaenoic acid (EPA) and docosahexaenoic acid (DHA), the preferred omega fatty acids of the present invention are singly or combined selected from EPA and DHA. ALA is considered an essential fatty acid, while DHA and EPA are considered conditionally essential. The combined DHA and EPA is in an amount of between 0.6 to 15 g i.e. an amount between the WHO RDA for each omega-3 fatty acid and 75% of the MTD of combined DHA and EPA and any value therebetween. Derivatives of omega-3 fatty acids are also encompassed in the present invention such as esters, especially ethyl esters and other alkyl derivatives, solvates thereof, pharmaceutically acceptable salt thereof, or combinations thereof as mentioned hereinbefore.

B Vitamins

Thus, the present invention involves the use of one or more B vitamins with omega-3 fatty acids. In one embodiment, the first B vitamin is selected from Vitamin $B_6$, Vitamin $B_{12}$ and a folate species and derivatives thereof, salts and free acids thereof. In one embodiment, the composition is for use in combination with a composition comprising one or more alternative B vitamins.

In one embodiment, the methods, medicaments and/or compositions of the present invention may further comprise a second B vitamin. The second B vitamin may be selected from a folate species, Vitamin $B_6$ and Vitamin $B_{12}$ and derivatives thereof.

In one embodiment, the method and compositions of the invention further comprise use of a third B Vitamin. In one embodiment, the third B vitamin is selected from Vitamin $B_6$, Vitamin $B_{12}$ and a folate species and derivatives thereof.

In one embodiment the methods and/or compositions of the present invention comprise use of a combination of three or more B vitamins with omega-3 fatty acids, said combination comprising a Vitamin $B_6$ species, a Vitamin $B_{12}$ species, and a folate species. Thus, the present invention includes the administration of a combination of B vitamins with omega-3 fatty acids, either comprised in the same composition or administered separately. In one embodiment, there is provided a combination of B vitamins e.g. a Vitamin $B_6$ species, a Vitamin $B_{12}$ species, and a folate species and an omega-3 fatty acid for use in the treatment of cognitive disorders, as described in more detail herein. The vitamin species may be compounds as described elsewhere herein in relation to vitamins B6 and B12 and to folate, and may be as the free compound or derivatised e.g. as a salt thereof. In this specification, references to vitamin B6 and vitamin B12 therefore include reference to vitamin B6 species and vitamin B12 species, respectively.

In one embodiment, the invention comprises administering folic acid (pteroylmonoglutamate) to a subject either alone or in combination with other agents described herein. Folic acid is also known as vitamin $B_9$ or folacin. In one embodiment, the method comprises administering a compound selected from folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or a combination of two or more thereof. In one embodiment of the present invention, folic acid or folate in one of its forms described above may be present in a composition and/or administered to a subject in an amount ranging from about 0.1 mg to about 10 mg. In another embodiment, Vitamin $B_{12}$ may be present in the amount ranging from about 0.01 mg to about 1.5 mg. In another embodiment, Vitamin $B_{12}$ may be present in the amount ranging from about 0.4 mg to about 0.9 mg. In one embodiment of the present invention, Vitamin $B_{12}$ may be present in the amount of about 0.8 mg. In one embodiment, the invention comprises administering Vitamin $B_{12}$ either alone or in combination with other B vitamins. Vitamin $B_{12}$ is also known as cobalamin and can be converted to the active coenzymes, methylcobalamin and 5'-deoxyadenosylcobalamin. These coenzymes are necessary for folic acid metabolism, removal of homocysteine, and myelin synthesis. For example, methylcobalamin catalyzes the demethylation of a folate cofactor. A lack of demethylation may result in deficiency of the folate from required for DNA synthesis. Deoxyadenosylcobalamin is the coenzyme for the conversion of methylmalonyl-CoA to succinyl-CoA, and is required for the entry of odd-chain fatty acids into the citric acid cycle. Vitamin $B_{12}$, along with pyridoxine and folic acid in implicated in the proper metabolism of homocysteine. Vitamin $B_{12}$ is available, for example, ascyanocobalamin, methylcobalamin, hydroxocobalamin and adenosylcobalamin.

One embodiment of the compositions and methods of the present invention may include Vitamin $B_{12}$. In one embodiment of the present invention, Vitamin $B_{12}$ may be present in a composition and/or administered to a subject in an amount ranging from about 0.01 mg to about 1.5 mg. In another embodiment, Vitamin $B_{12}$ may be present in the amount ranging from about 0.2 mg to about 1 mg. In another embodiment, Vitamin $B_{12}$ may be present in the amount ranging from about 0.4 mg to about 0.8 mg. In one embodiment of the present invention, Vitamin $B_{12}$ may be present in the amount of about 0.5 mg. In one embodiment, the Vitamin $B_{12}$ is cyanocobalamin.

In one embodiment, the invention comprises administering Vitamin $B_6$ either alone or in combination with other B vitamins. Vitamin $B_6$ may be present in a composition and/or administered to a subject in an amount ranging from about 0.5 mg to about 40 mg. In another embodiment, Vitamin $B_6$ may be present in the amount ranging from about 15 mg to about 30 mg. In another embodiment, Vitamin $B_6$ may be present in the amount ranging from about 15 mg to about 25 mg. In one embodiment of the present invention, Vitamin $B_{12}$ may be present in the amount of about 20 mg.

In one embodiment, additional choline is administered to a subject. Choline may be comprised in for example a phospholipid such as phosphatidylcholine. In one embodiment, betaine is administered to the subject. Choline is a pre-cursor to betaine in the human body. Betaine is a substrate which acts in the conversion of homocysteine to methionine.

Pharmaceutically Acceptable Carriers

The present invention includes pharmaceutical compositions comprising an omega-3 fatty acid and B vitamins (B6, B9 also known as folate, and B12) as described herein. The compositions may consist of the omega-3 fatty acid (e.g. EPA and DHA in combination) and the vitamins and one or more pharmaceutically acceptable excipients and/or carriers.

In one embodiment, the composition comprises a pharmaceutically acceptable carrier. The pharmaceutically acceptable carriers useful in the methods disclosed herein are conventional. Remington's Pharmaceutical Sciences, by E. W. Martin, Mack Publishing Co, Easton, PA, 15th Edition (1975), describes compositions and formulations suitable for pharmaceutical delivery of various agents.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Typically, omega-3 fatty acids are formulated as oils in soft capsules, however other forma such as water-soluble formulations, gels and stabilized powders are also encompassed within the scope of the invention.

In a preferred embodiment, the compositions of the invention are for oral administrations and are e.g. solid dosage forms. Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid, for example; b) binders such as carboxymethylcellulose, alginates, gelatin, polyvinylpyrrolidone, sucrose and acacia, for example; c) humectants such as glycerol, for example; d) disintegrating agents such as agar-agar, calcium carbonate, potato or tapioca starch, alginic acid, certain silicates and sodium carbonate, for example; e) solution retarding agents such as paraffin, for example; f) absorption accelerators such as quaternary ammonium compounds, for example; g) wetting agents such as cetyl alcohol and glycerol monostearate, for example; h) absorbents such as kaolin and bentonite clay for example and i) lubricants such as talc, calcium stearate, magnesium stearate, solid polyethylene glycols, sodium lauryl sulfate and mixtures thereof, for example. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

The compositions of the invention may be in the form of oral formulations, and consequently the methods of the invention comprise oral administration of the agents e.g. omega-3 fatty acids, choline, betaine and/or B vitamin(s). Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, capsules, pills, and granules can be prepared with coatings and shells such as enteric coatings and other coatings such as multiple coatings, for example, well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions which can be used include polymeric substances and waxes.

Alternatively, the agents described herein e.g. omega-3 fatty acids, B vitamin(s), betaine and/or choline may be comprised in a liquid dosage form. Liquid dosage forms for oral administration include pharmaceutically acceptable emulsions, solutions, suspensions, syrups and elixirs.

In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

In one embodiment, the mode of administration of the agent of the invention may be intravenous, inter-arterial, intramuscular or subcutaneous injection. In one embodiment, the omega-3 fatty acids and B vitamins may be administered intramuscularly, e.g. Vitamin $B_{12}$.

Materials and Methods

Participants

This study was conducted as a part of the VITACOG trial, 'Homocysteine and B vitamins in cognitive impairment', and was carried out according to the principles of the Declaration of Helsinki and received approval of the Oxfordshire NHS research ethics committee A (COREC 04/Q1604/100). All participants gave their written informed consent. The study protocol and participants, along with inclusion and exclusion criteria, have been described in detail elsewhere (Smith et al, PLOS One 2010; 5 (9); e12244.doi10.1371/journal.pone. 0012244). In short, 646 patients above 70 years of age with a diagnosis of MCI were assessed for eligibility. After randomization of eligible subjects, and some withdrawals, 133 started treatment with TrioBe Plus® (0.8 mg folic acid, 0.5 mg vitamin $B_{12}$, and 20 mg vitamin $B_6$, specifically 0.8 mg folic acid, 0.5 mg cyanocobalamin and 20 mg pyridoxine HCl) while 133 received placebo for a duration of 24 months. Participants were only included in this study if brain atrophy data was available. 168 patients completed the study with technically suitable MRI scans at baseline and follow-up. Of these, 85 were in the B vitamin group, and 83 were in the placebo group.

MRI Scans

The MRI protocol used in the VITACOG study has been described in detail elsewhere (Smith et al referenced above). In short, baseline and follow-up volumetric cranial MRI scans were carried out at the Oxford Centre for Clinical Magnetic Resonance Research using a 1.5 T MRI system (Sonata; Siemens Medical Solutions, Erlangen, Germany). Whole brain atrophy per year was estimated from MR images taken at baseline and follow-up, using the fully automated SIENA protocol which provides accuracy and robustness. Normalized brain volume at baseline was estimated from a single image using a cross-sectional method (SIENAX), and used as a covariate in the statistical analyses.

Plasma Assays

Plasma was prepared from non-fasting blood samples collected at baseline and after 24 months of intervention. Total fatty acids were analyzed by gas chromatography coupled to mass spectrometry (GC-MS), using a modified in situ transesterification protocol for fatty acid methyl ester preparation (Supplemental material). Fatty acid concentrations were expressed as absolute values (µM), unless otherwise stated. The coefficients of variance for DHA and EPA were 4.7% and 3.9%, respectively, and <10% for the remaining fatty acids (Table 1). ApoE genotype, plasma tHcy, folate, and vitamin $B_{12}$ were analyzed as previously described (Vogiatzoglou et al Neurology, 2008; 71 (11): 826-32).

TABLE 1

Fatty acids analyzed by GC-MS[1]

| Name | Formula | RT (min) | SIM masses | CV (%) |
|---|---|---|---|---|
| Lauric acid | 12:0 | 2.0 | [74, 87] | 9.2 |
| Myristic acid | 14:0 | 3.1 | [74, 87] | 4.9 |
| Palmitic acid | 16:0 | 4.8 | [74, 87] | 6.0 |
| Palmitoleic acid | 16:1 | 5.2 | [55, 74] | 6.2 |
| Heptadecanoic acid (IS) | 17:0 | 5.9 | [74, 87] | NA |
| Stearic acid | 18:0 | 7.2 | [74, 87] | 6.9 |
| Oleic acid | 18:1 | 7.6 | [55, 74] | 4.7 |
| Linoleic acid | 18:2n-6 | 8.3 | [55, 67] | 4.5 |
| γ-Linolenic acid | 18:3n-6 | 8.8 | [67, 79] | 6.7 |
| α-Linolenic acid | 18:3n-3 | 9.3 | [67, 79] | 4.7 |
| Heneicosanoic acid (IS) | 21:0 | 11.4 | [74, 87] | NA |
| Dihomo-γ-linolenic acid | 20:3n-6 | 11.7 | [67, 79] | 4.1 |
| Arachidonic acid | 20:4n-6 | 12.1 | [67, 79] | 4.8 |
| Eicosapentaenoic acid | 20:5n-3 | 13.4 | [79, 91] | 3.9 |
| Docosahexaenoic acid | 22:6n-3 | 16.2 | [67, 79] | 4.7 |

[1]CV, Coefficient of variation; GC-MS, Gas chromatography-mass spectrometry; RT retention time; SIM, selective ion monitoring.

Statistical Analysis

IBM SPSS for Windows, version 20, was used for all statistical analyses (IBM Corp., Armonk, NY, USA). Skewed fatty acids were normalized using their natural logarithms. Unless otherwise stated, fatty acid concentrations at baseline were used for statistical analyses. The main outcome in this study was to investigate the effect of B vitamin treatment on brain atrophy rates, based on baseline omega-3 fatty acid status. Analyses of variance, were used to further examine associations between the fatty acid variables and tHcy and brain atrophy. Two correction models were used. Model A was adjusted for age, sex, and initial brain volume, while model B also adjusted for plasma tHcy, ApoE status, education level, and baseline levels of diastolic blood pressure, triglyceride concentration, and creatinine concentration. When the entire study population was included in the analysis, tHcy measured at follow-up was used as covariate since this measure most likely represents the average tHcy during the trial. When the analysis was confined to the placebo group, tHcy at baseline was used. The baseline fasting glucose concentration was also investigated, but since it was not associated with brain atrophy rate, it was excluded as a covariate in subsequent analyses.

Differences between atrophy rate in the placebo and B vitamin groups were assessed using Student's t test, while brain atrophy rates according to different levels of fatty acids (tertiles), were analyzed using ANCOVA. Where an ANCOVA indicated significant differences between tertiles, Bonferroni corrected post hoc comparisons were made between the lowest and the two higher tertiles. A tHcy threshold of 11.3 µM was used to separate into low and high tHcy. This value corresponds to the median baseline tHcy concentration of the study population, above which previous studies revealed that the beneficial effect of B vitamin treatment on global and regional brain atrophy and cognitive decline was confined. $P<0.05$ was considered statistically significant in all analyses.

Example 1

Relevant baseline characteristics of the study participants are summarized in Table 2. As previously reported (Smith et al, PLOS One 2010; 5 (9); e12244.doi10.1371/journal.pone. 0012244) the baseline characteristics in the active and placebo groups were similar. In addition, baseline concentrations of omega-3 fatty acids were not significantly different between the treatment groups.

TABLE 2

Characteristics of participants in the VITACOG study[1].

| | ALL[2] (N = 168) Mean | PLACEBO (N = 83) Mean | ACTIVE (N = 85) Mean |
|---|---|---|---|
| Age, years | 76.3 (75.5-77.1) | 75.8 (74.8-76.9) | 76.8 (75.5-78.1) |
| Women, n (%) | 102 (60.7) | 52 (62.7) | 50 (58.9) |
| Brain volume, (mL) | 1381 (1368-1393) | 1377 (1361-1393) | 1384 (1364-1405) |
| BMI, (kg/m$^2$) | 25.7 (25.1-26.4) | 26.1 (25.1-27.1) | 25.3 (24.5-26.1) |
| Systolic BP, (mmHg) | 148 (144-152) | 147 (143-152) | 149 (142-155) |
| Diastolic BP, (mmHg) | 80 (78-82) | 81 (78, 84) | 80 (77-82) |
| Depression score, (GDS) | 6.6 (5.8-7.4) | 7.6 (6.4-8.9) | 5.5 (4.5-6.4) |
| Alcohol consumption, (units/week) | 8.8 (6.6-11.0) | 8.8 (4.9-12.7) | 8.8 (6.6-10.9) |
| Anti-diabetic drugs, n (%) | 14 (8.3) | 10 (12) | 4 (4.7) |
| Use of NSAID, n (%) | 30 (17.9) | 12 (14.5) | 18 (21.2) |
| Smoker, anytime, n (%) | 81 (48.2) | 43 (51.8) | 38 (44.7) |
| Use of vitamins, n (%) | 31 (18.5) | 17 (20.5) | 14 (16.5) |
| Use of fish oils, omega-3, n (%) | 67 (39.9) | 31 (37.3) | 36 (42.4) |
| ApoE carriers, n (%) | 51 (30.4) | 29 (35) | 22 (25.9) |
| tHcy, baseline[3] (μM) | 11.3 (10.7-11.8) | 11.1 (10.4-11.9) | 11.4 (10.6-12.2) |
| tHcy, follow up[3] (μM) | 10.3 (9.8-10.9) | 12.1 (11.3-12.9) | 8.8 (8.3-9.3) |
| DHA, baseline[3] (μM) | 288 (268-310) | 296 (269-325) | 281 (251-314) |
| DHA, follow up[3] (μM) | 282 (263-303) | 286 (258-316) | 279 (252-309) |
| EPA, baseline[3] (μM) | 179 (161-200) | 181 (155-212) | 177 (153-206) |
| EPA, follow up[3] (μM) | 179 (161-199) | 179 (153-208) | 181 (156-209) |
| Vitamin B$_{12}$, baseline[3] (μM) | 331 (313-351) | 340 (316-367) | 323 (295-353) |
| Vitamin B$_{12}$, follow up[3] (μM) | 499 (462-538) | 380 (346-417) | 658 (607-712) |
| Folate, baseline[3] (μM) | 23.8 (21.4-26.5) | 23.8 (20.8-27.2) | 23.8 (20.2-28.1) |
| Folate, follow up[3] (μM) | 44.7 (38.8-51.5) | 24.7 (20.9-29.1) | 81.8 (73.2-91.4) |

[1]ApoE, apolipoprotein E; BP, blood pressure; DHA, docosahexaenoic acid; EPA, eicosapentaenoic acid; GDS, depression score; NSAID, non-steroidal anti-inflammatory drug; tHcy, total homocysteine. Unless otherwise stated, values are expressed as means with 95% confidence intervals.
[2]Samples with available brain atrophy rate data.
[3]Geometric mean.

Example 2

The correlations at baseline and the effect of B vitamin intervention on fatty acid concentrations were investigated. Since previous studies have reported associations between omega-3 fatty acids and homocysteine concentrations (Mehmetoglu et al Asia Pac J Clin Nutr 2012; 21 (4): 519-15. Huang et al Nutrition 2011; 27 (9): 863-7 doi 10.1016/j.nut.2010.12.011), correlation analyses at baseline were performed. We found a significant negative correlation between the tHcy and DHA (r=−0.21, P=0.007) and EPA (r=−0.18, P=0.020). To investigate whether B vitamin treatment affected omega-3 concentrations in plasma, we compared the changes in fatty acid concentrations over 24 months in the treated group vs placebo. We found no statistically significant effect of B vitamin treatment on DHA or EPA concentrations, expressed either in absolute (Table 2) or relative concentrations (data not shown).

Example 3

Partial correlation analyses were performed to investigate associations between absolute fatty acid concentrations and brain atrophy rates in the whole study group and stratified by treatment group (Table 3). In the total study group, only DHA and EPA showed significant negative correlations with brain atrophy rates in both models.

TABLE 3

Plasma fatty acid concentrations at baseline as predictors of yearly brain atrophy rate[1].

| | ALL[2] | | PLACEBO | | ACTIVE | |
|---|---|---|---|---|---|---|
| | Model A | Model B | Model A | Model B | Model A | Model B |
| 12:0 | −0.04 | −0.05 | −0.08 | −0.07 | −0.04 | −0.03 |
| 14:0 | −0.05 | −0.05 | −0.06 | −0.01 | −0.08 | −0.13 |
| 16:0 | −0.09 | −0.11 | 0.00 | 0.04 | −0.18 | −0.22 |
| 16:1 (Palmitoleic) | −0.10 | −0.12 | 0.02 | −0.01 | −0.20 | −0.27* |
| 18:0 | −0.10 | −0.10 | −0.07 | −0.01 | −0.14 | −0.17 |
| 18:1 (Oleic) | −0.09 | −0.12 | 0.01 | 0.05 | −0.19 | −0.27* |
| 18:2n-6 | −0.14 | −0.14 | −0.08 | −0.04 | −0.21 | −0.17 |
| 18:3n-3 | −0.05 | −0.06 | −0.00 | 0.05 | −0.13 | −0.13 |
| 18:3n-6 | −0.02 | −0.00 | 0.06 | 0.08 | −0.03 | −0.06 |
| 20:3n-6 | −0.08 | −0.07 | 0.06 | 0.07 | −0.17 | −0.21 |
| 20:4n-6 | −0.13 | −0.15 | 0.05 | 0.05 | −0.25* | −0.31* |

TABLE 3-continued

Plasma fatty acid concentrations at baseline as predictors of yearly brain atrophy rate[1].

|  | ALL[2] | | PLACEBO | | ACTIVE | |
| --- | --- | --- | --- | --- | --- | --- |
|  | Model A | Model B | Model A | Model B | Model A | Model B |
| 20:5n-3 (EPA) | −0.16* | −0.16* | −0.13 | −0.06 | −0.23* | −0.27* |
| 22:6n-3 (DHA) | −0.22* | −0.23* | −0.15 | −0.07 | −0.34* | −0.36* |
| Total FA | −0.12 | −0.16 | −0.04 | 0.00 | −0.22 | −0.27* |

[1]Partial correlation coefficients adjusted for age, sex, and initial brain volume (Model 1) or additionally ApoE status, education level, diastolic blood pressure at baseline, triglyceride concentration at baseline, creatinine concentration at baseline, and total homocysteine at follow up (Model 2). Statistically significant correlations ($P < .05$) are highlighted in bold with an asterisk (*).
[2]Samples with available brain atrophy rate data.

Analysis of the placebo group did not reveal any statistically significant correlations between brain atrophy rates and fatty acids. In the active treatment group, the correlations between brain atrophy rates and DHA and EPA were significant using both models of correction. In addition, palmitic-(16:1n-7), oleic-(18:1n-9), arachidonic (20:4n-6), and total fatty acid concentrations significantly correlated with atrophy rates in subjects receiving B vitamins.

Since the concentration of total fatty acids might explain some of the associations found with individual fatty acids, correlation analysis was also performed using relative amounts of fatty acids (Table 4). Only DHA was significantly associated with brain atrophy rates (r=−0.28, P=0.018, model B). EPA was not significant correlated with brain atrophy rates using this model, but showed a stronger association (r=−0.20, P=0.099) compared with palmitic-, oleic-, and arachidonic acid.

TABLE 4

Correlation between yearly brain atrophy rate and relative fatty acids concentrations at baseline[1]

|  | ALL[2] | | PLACEBO | | ACTIVE | |
| --- | --- | --- | --- | --- | --- | --- |
|  | Model A | Model B | Model A | Model B | Model A | Model B |
| 12:0 | 0.00 | 0.00 | −0.08 | −0.08 | 0.04 | 0.06 |
| 14:0 | 0.02 | 0.05 | −0.05 | −0.01 | 0.06 | 0.06 |
| 16:0 | 0.11 | 0.12 | 0.14 | 0.14 | 0.08 | 0.08 |
| 16:1n-7 | −0.04 | −0.06 | 0.05 | −0.01 | −0.11 | −0.18 |
| 18:0 | 0.05 | 0.08 | −0.09 | −0.02 | 0.16 | 0.12 |
| 18:1n-9 | 0.03 | 0.05 | 0.10 | 0.11 | −0.06 | −0.06 |
| 18:2n-6 | −0.01 | −0.02 | −0.07 | −0.08 | 0.05 | 0.14 |
| 18:3n-3 | 0.03 | 0.02 | 0.02 | 0.06 | −0.01 | 0.01 |
| 18:3n-6 | 0.08 | 0.10 | 0.10 | 0.08 | 0.16 | 0.10 |
| 20:3n-6 | 0.01 | 0.05 | 0.12 | 0.09 | 0.01 | −0.02 |
| 20:4n-6 | −0.02 | −0.04 | 0.10 | 0.05 | −0.07 | −0.15 |
| 20:5n-3 | −0.12 | −0.12 | −0.13 | −0.06 | −0.15 | −0.20 |
| 22:6n-3 | −0.17* | −0.18* | −0.14 | −0.08 | −0.25* | −0.28* |

[1]Partial correlation coefficients adjusted for age, sex, and initial brain volume (Model 1) or additionally ApoE status, education level, diastolic blood pressure at baseline, triglyceride concentration at baseline, creatinine concentration at baseline, and total homocysteine at follow up (Model 2). Statistically significant correlations (P < 0.05) are highlighted in bold with an asterisk (*).
[2]Samples with available brain atrophy rate data.

Example 4

The effect of omega-3 concentrations at baseline on B vitamin slowing of brain atrophy rate was investigated. Annual atrophy rates in the placebo and B vitamin groups were assessed by tertiles of baseline DHA and EPA concentrations (FIG. 1). While there were no significant differences between the placebo group and subjects receiving B vitamins in the lowest DHA (−8.9%, P=0.60) or EPA (−2.5%, P=0.88) tertiles, the active treatment group had significantly lower brain atrophy rates in subjects in the top two tertiles of DHA and EPA. In the top tertile of DHA, annual brain atrophy rate was reduced by 43.9% compared with placebo (P=0.009). The corresponding figure for EPA was 38.9% (P=0.020).

Figure 2:
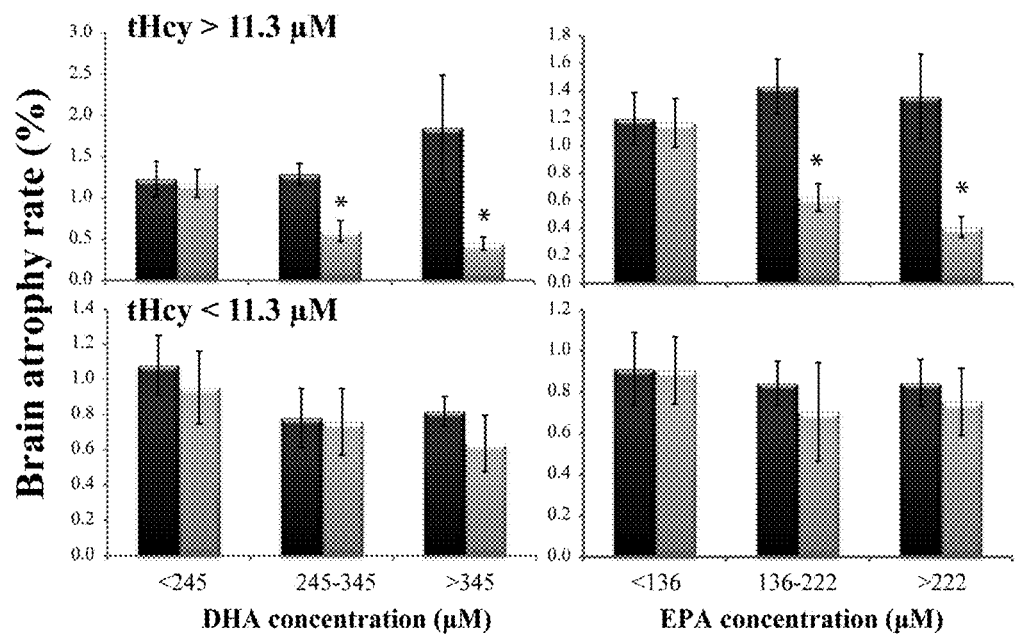
FIG. 2 shows the comparison of annual brain atrophy rate between placebo (black) and B vitamin treatment (gray) (+/−SEM) based on tertiles of baseline DHA (left panels) and EPA (right panels) in subjects with baseline tHcy levels above 11.3 μM (top) and below 11.3 μM (bottom). An asterisk (*) indicates a significant difference between groups as assessed with independent t-tests (P<0.05).

Previous reports have noted that the treatment response on brain atrophy rates and cognitive measurements were related to the baseline concentration of homocysteine (Smith et al, PLOS One 2010; 5 (9); e12244.doi10.1371/journal.pone. 0012244, De Jager et al Int J geriatr Psychiatry 2012; 27 (6); 592-600). The effect of baseline DHA and EPA concentrations on the response to B vitamin treatment was therefore investigated in subjects with baseline homocysteine above or below a cut-off value of 11.3 μM. In the high baseline tHcy group, B vitamin treatment reduced brain atrophy rate by 53% (P=0.001) and 76% (P=0.001) in subjects with middle and top tertile DHA concentrations, respectively, compared with the placebo group (FIG. 2). For EPA, there was a significant reduction in atrophy rate by B vitamins in subjects with middle (56% reduction, P=0.002), and top tertiles (70% reduction, P=0.002) of EPA (FIG. 2). B vitamin treatment had no statistically significant effect compared with placebo in subjects with baseline tHcy concentrations below 11.3 μM, independent of DHA or EPA concentration.

General linear models were used to investigate whether increasing baseline plasma DHA and EPA concentrations had protective effects on the rate of brain atrophy in the placebo and active treatment groups (Table 5). In the active treatment group, moderate and high DHA and EPA concentrations were associated with slower rates of atrophy compared with subjects in the lowest fatty acid tertiles.

TABLE 5

General linear model of brain atrophy rates in tertiles of DHA and EPA[1].

|  |  | PLACEBO | | | | ACTIVE | | | |
| --- | --- | --- | --- | --- | --- | --- | --- | --- | --- |
|  |  | N | BAR[2] | %[3] | P[4] | N | BAR[2] | %[3] | P[4] |
| DHA |  |  |  |  |  |  |  |  |  |
| Model A | <245 µM | 24 | 1.13 |  |  | 31 | 1.04 |  |  |
|  | 245-345 µM | 32 | 1.10 | −3.0 | 1.000 | 24 | 0.70 | −33 | 0.112 |
|  | >345 µM | 27 | 0.99 | −13 | 0.830 | 29 | 0.56 | −46 | 0.012* |
| Model B | <245 µM | 24 | 1.07 |  |  | 31 | 1.08 |  |  |
|  | 245-345 µM | 31 | 1.09 | 1.3 | 1.000 | 23 | 0.62 | −42 | 0.034* |
|  | >345 µM | 27 | 1.04 | −3.2 | 1.000 | 27 | 0.56 | −48 | 0.014* |
| EPA |  |  |  |  |  |  |  |  |  |
| Model A | <136 µM | 26 | 1.08 |  |  | 29 | 1.01 |  |  |
|  | 136-222 µM | 29 | 1.14 | 5.7 | 1.000 | 27 | 0.68 | −33 | 0.118 |
|  | >222 µM | 28 | 1.00 | −7.0 | 1.000 | 28 | 0.62 | −38 | 0.076 |
| Model B | <136 µM | 26 | 0.99 |  |  | 29 | 1.08 |  |  |
|  | 136-222 µM | 28 | 1.12 | 13 | 0.934 | 26 | 0.68 | −36 | 0.072 |
|  | >222 µM | 28 | 1.08 | 8.8 | 1.000 | 26 | 0.53 | −51 | 0.018* |

[1]BAR, brain atrophy rate; DHA, docosahexaenoic acid; EPA, eicosapentaenoic acid.
[2]Expressed as percent brain whole brain reduction per year, adjusted for age, sex, and initial brain volume (Model 1) or additionally ApoE status, education level, diastolic blood pressure at baseline, triglyceride concentration at baseline, creatinine concentration at baseline, and total homocysteine at follow up (Model 2).
[3]Percent change compared to the lowest tertile.
[4]Bonferroni corrected statistical significance level (P < 0.05) are highlighted in bold with an asterisk (*).

Example 5

The impact of baseline omega-3 concentrations on atrophy rate according to tHcy status was studied. Since the main effect of B vitamin treatment is to lower tHcy, the effect of increasing baseline omega-3 concentrations was investigated in the entire study group, based on tHcy concentration at the end of the study. Increasing amounts of omega-3 were associated with decreasing rates of brain atrophy in subjects with tHcy below 11.3 µM at follow-up (Table 6). In subjects with high tHcy (<11.3 µM) at follow-up, there were no significant differences in brain atrophy rates between tertiles of baseline DHA or EPA.

An analysis of brain atrophy rates in the placebo group was conducted to further investigate the impact of homocysteine on the effects of omega-3 fatty acids. The placebo group was divided by baseline tHcy. There were no significant differences between the high and low tHcy groups in the bottom omega-3 tertiles (data not shown). The brain atrophy rate in subjects with moderate or high DHA concentrations were significantly lower in subjects with tHcy <11.3 µM.

In summary, the rate of whole-brain atrophy significantly correlated with DHA (r=−0.358, P=0.002) and EPA (r=−0.265, P=0.023) in the active treatment group, but not in the placebo group (DHA r=−0.071, P=0.553; EPA r=−0.056, P=0.636). B vitamin treatment did not have any significant

TABLE 6

General linear model of brain atrophy rates in tertiles of DHA and EPA based on tHcy status at follow-up.

|  |  | LOW | | | | HIGH | | | |
| --- | --- | --- | --- | --- | --- | --- | --- | --- | --- |
|  |  | N | BAR[2] | %[3] | P[4] | N | BAR[2] | %[3] | P[4] |
| DHA |  |  |  |  |  |  |  |  |  |
| Model A | <245 µM | 34 | 1.09 |  |  | 21 | 1.08 |  |  |
|  | 245-345 µM | 28 | 0.71 | −34 | 0.032* | 27 | 1.12 | 7.7 | 1.000 |
|  | >345 µM | 46 | 0.68 | −37 | 0.006* | 10 | 1.13 | 8.6 | 1.000 |
| Model B | <245 µM | 34 | 1.20 |  |  | 21 | 1.06 |  |  |
|  | 245-345 µM | 28 | 0.70 | −36 | 0.006* | 26 | 1.14 | 5.7 | 1.000 |
|  | >345 µM | 44 | 0.62 | −43 | <0.001* | 10 | 1.08 | 0.4 | 1.000 |
| EPA |  |  |  |  |  |  |  |  |  |
| Model A | <136 µM | 33 | 1.07 |  |  | 22 | 1.02 |  |  |
|  | 136-222 µM | 33 | 0.73 | −30 | 0.048* | 23 | 1.19 | 18 | 0.858 |
|  | >222 µM | 42 | 0.69 | −33 | 0.020* | 13 | 1.11 | 9.5 | 1.000 |
| Model B | <136 µM | 33 | 1.14 |  |  | 22 | 0.98 |  |  |
|  | 136-222 µM | 32 | 0.76 | −27 | 0.034* | 22 | 1.20 | 11 | 0.672 |
|  | >222 µM | 41 | 0.63 | −40 | 0.002* | 13 | 1.13 | 4.3 | 1.000 |

[1]BAR, brain atrophy rate; DHA, docosahexaenoic acid; EPA, eicosapentaenoic acid.
[2]Expressed as percent brain whole brain reduction per year, adjusted for age, sex, and initial brain volume (Model 1) or additionally ApoE status, education level, diastolic blood pressure at baseline, triglyceride concentration at baseline, creatinine concentration at baseline, and total homocysteine at follow up (Model 2).
[3]Percent change compared to the lowest fatty acid tertile.
[4]Bonferroni corrected statistical significance level (P < 0.05) are highlighted in bold with an asterisk (*).

effect on the omega-3 levels. When analysed by tertiles of baseline omega-3 levels, B-vitamin treatment reduced atrophy rates by 43.9% in subjects with high DHA (P=0.009), compared with placebo. For EPA, this figure was 38.9% (P=0.020). B-vitamin treatment had no significant effect among subjects in the lowest tertile of DHA, or of EPA. The mean difference in atrophy rate between the lowest and highest tertile of DHA was 48.0% (P=0.007) in the active group. The corresponding figure for EPA was 50.8% (P=0.009). Increasing levels of DHA and EPA had no significant influence on the atrophy rate in the placebo group.

Example 6

Figure 3:
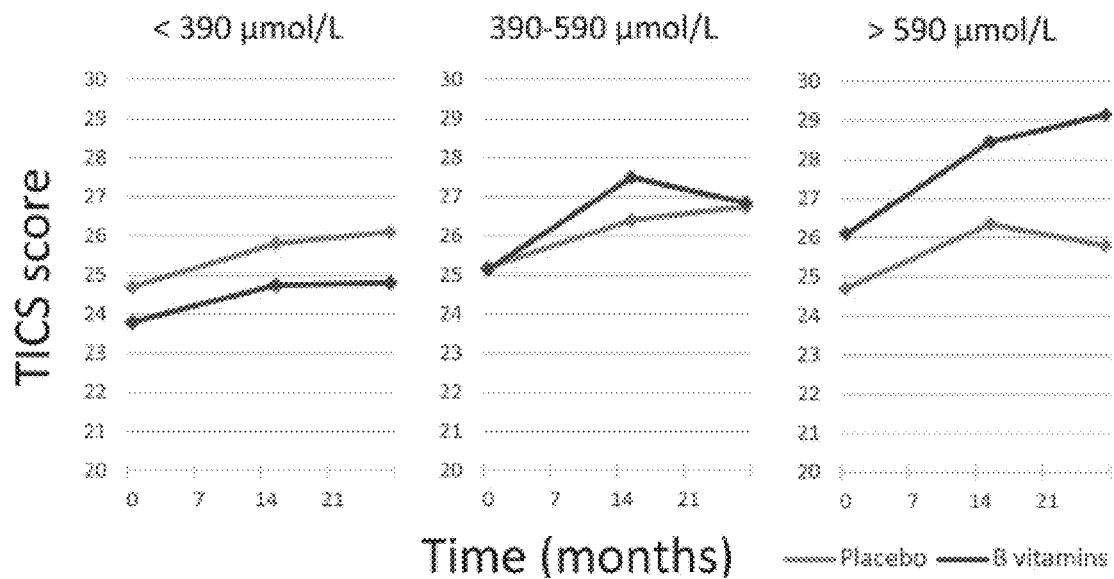
FIG. 3 shows the mean scores in a cognitive test TICS (Telephone Interview for Cognitive Status) in those participants in VITACOG with Mild Cognitive Impairment who received placebo (blue) compared with those who were treated with B vitamins (red) at three different baseline blood concentrations of the combination of two omega-3 fatty acids (DHA and EPA).

FIG. 3 shows the mean scores in a cognitive test called TICS (Telephone Interview for Cognitive Status) in those participants in VITACOG with Mild Cognitive Impairment who received placebo (blue) compared with those who were treated with B vitamins (red) at three different baseline blood concentrations of the combination of two omega-3 fatty acids (DHA and EPA). Only participants with the highest blood levels of omega-3 fatty acids showed improved test performance after 24 months when treated with B vitamins.

Figure 4:
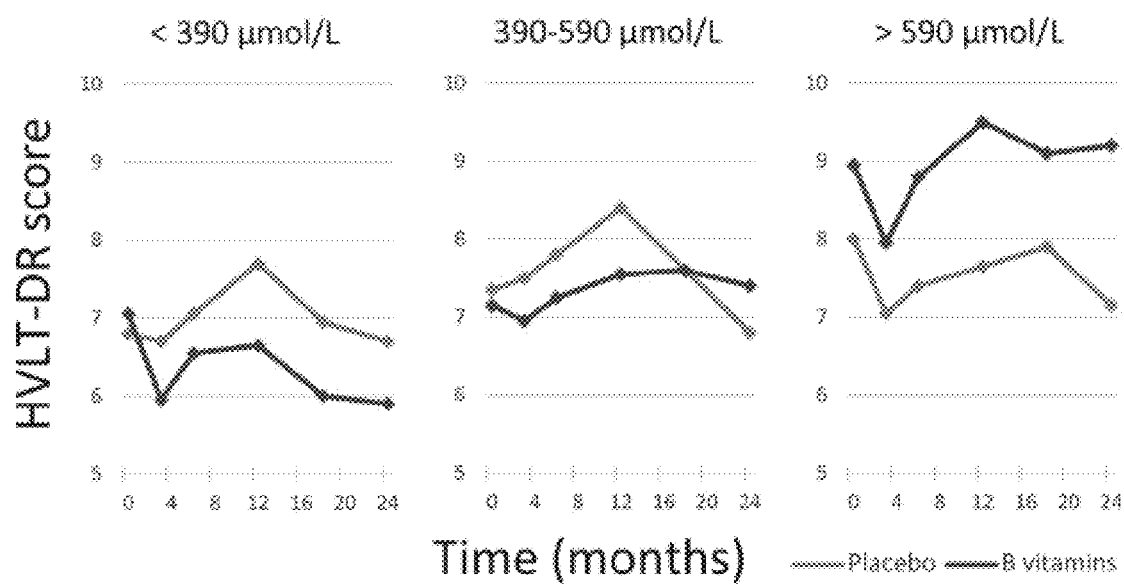
FIG. 4 shows the mean scores in a test of episodic memory (Delayed Recall part of the Hopkins Verbal Memory Test) in those participants in VITACOG with Mild Cognitive Impairment who received placebo (blue) compared with those who were treated with B vitamins (red) at three different baseline blood concentrations of the combination of two omega-3 fatty acids (DHA and EPA).

FIG. 4 shows the mean scores in a test of episodic memory (Delayed Recall part of the Hopkins Verbal Memory Test) in those participants in VITACOG with Mild Cognitive Impairment who received placebo (blue) compared with those who were treated with B vitamins (red) at three different baseline blood concentrations of the combination of two omega-3 fatty acids (DHA and EPA). Only participants with the highest blood levels of omega-3 fatty acids maintained their memory performance after 24 months when treated with B vitamins.

The combined data presented herein suggests that B vitamin treatment significantly reduced the brain atrophy rate only in subjects with moderate or high plasma levels of long-chain omega-3 fatty acids. Similarly, increasing levels of DHA or EPA had no significant effect on the brain atrophy rate in subjects receiving placebo, suggesting that a controlled tHcy status might be required for beneficial effects of omega-3 fatty acids in cognitive decline, dementia, and Alzheimer's disease.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for delaying or preventing the onset of increased brain atrophy associated with mild cognitive impairment in a human subject compared to cognitively healthy controls, wherein the human subject:
   i) has a total plasma level of DHA below about 250 µM and a total plasma level of EPA below about 140 µM;
   ii) has a baseline homocysteine level above 11.3 µmol/L; and
   iii) is 50 years old or over;
the method comprising administering to the human subject the following:
   (i) one or more of DHA, EPA or a derivative thereof, in an amount sufficient to increase the circulating total plasma concentration of DHA and EPA to greater than about 590 µmol/L;
   (ii) a folate species in an amount of from 0.5 mg to 1.5 mg;
   (iii) a vitamin B12 species in an amount of 0.09 mg to 2 mg; and
   (iv) a vitamin B6 species in an amount of from 15 mg to 30 mg.

2. The method of claim 1, wherein the total fatty acid daily dosage of DHA, EPA or a derivative thereof is from 1 g to 10 g.

3. The method according to claim 1, wherein the DHA or EPA is in the form of the free acid, a salt or an ester.

4. The method according to claim 1, wherein memory performance is maintained following 24 months of administration of the one or more of DHA, EPA or a derivative thereof, folate species, vitamin B12 species and vitamin B6 species.

5. A method of reducing the rate of brain atrophy in a human subject with mild cognitive impairment for:
   a) retarding the progression of mild cognitive impairment in the human subject;
   b) delaying or preventing the development of Alzheimer's disease in the human subject, wherein the human subject is at risk of developing Alzheimer's disease;
   c) reducing or retarding the rate of progression of, or retarding the onset of, Alzheimer's disease in the human subject, wherein the human subject is at risk of developing Alzheimer's disease;
   d) delaying the rate of loss of cognitive function in the human subject, wherein the human subject is at risk of developing loss of cognitive function,
   e) maintaining cognitive function in the human subject, wherein the human subject is at risk of developing atrophy-related loss of cognitive function; or
   f) maintaining memory function in the human subject, wherein the human subject is at risk of developing atrophy-related loss of cognitive function;
the method comprising administering to the human subject the following:
   (i) one or more of DHA, EPA or a derivative thereof, sufficient to increase the circulating total plasma concentration of DHA and EPA to greater than about 590 µmol/L;

(ii) a folate species in an amount of from 0.5 mg to 1.5 mg;
(iii) a vitamin B12 species in an amount of 0.09 mg to 2 mg; and
(iv) a vitamin B6 species in an amount of from 15 mg to 30 mg;
wherein the human subject:
i) has a total plasma level of DHA below about 250 μM and a total plasma level of EPA below about 140 μM;
iii) has a baseline homocysteine level above 11.3 μmol/L; and
iv) is 50 years old or over.

6. A method for reducing the rate of brain atrophy in a human subject with mild cognitive impairment for:
a) retarding the progression of the mild cognitive impairment;
b) delaying or preventing the development of Alzheimer's disease in the human subject, wherein the human subject is at risk of developing Alzheimer's disease;
c) reducing or retarding the rate of progression of, or retarding the onset of, atrophy-related Alzheimer's disease in the human subject, wherein the human subject is at risk of developing Alzheimer's disease;
d) delaying the atrophy-related rate of loss of cognitive function in the human subject, wherein the human subject is at risk of developing atrophy-related loss of cognitive function;
e) maintaining cognitive function in the human subject, wherein the human subject is at risk of developing atrophy-related loss of cognitive function; or
f) maintaining memory function in the human subject, wherein the human subject is at risk of developing atrophy-related loss of cognitive function;

the method comprising administering to the human subject the following:
(i) one or more omega-3 fatty acids, or a derivative thereof, in a daily dosage of from 0.4 g to 15 g;
(ii) a folate species in an amount of from 0.5 mg to 1.5 mg;
(iii) a vitamin B12 species in an amount of 0.09 mg to 2 mg; and
(iv) a vitamin B6 species in an amount of from 15 mg to 30 mg;
wherein the human subject:
i) has a total plasma level of DHA below about 250 μM and a total plasma level of EPA below about 140 μM;
iii) has a baseline homocysteine level above 11.3 μmol/L; and
iv) is 50 years old or over.

* * * * *